(12) United States Patent
Gorelik et al.

(10) Patent No.: US 9,233,107 B2
(45) Date of Patent: Jan. 12, 2016

(54) COMPOSITIONS AND METHODS FOR THE TREATMENT OF PROGRESSIVE MULTIFOCAL LEUKOENCEPHALOPATHY (PML)

(75) Inventors: Leonid Gorelik, Quincy, MA (US);
Margot Brickelmaier, Boxford, MA (US); Alexey Lugovskoy, Woburn, MA (US)

(73) Assignee: Biogen MA Inc., Cambridge, MA (US)

( * ) Notice: Subject to any disclaimer, the term of this patent is extended or adjusted under 35 U.S.C. 154(b) by 1642 days.

(21) Appl. No.: 12/678,011

(22) PCT Filed: Sep. 13, 2008

(86) PCT No.: PCT/US2008/010734

§ 371 (c)(1),
(2), (4) Date: Oct. 7, 2010

(87) PCT Pub. No.: WO2009/038684

PCT Pub. Date: Mar. 26, 2009

(65) Prior Publication Data

US 2013/0183289 A1    Jul. 18, 2013
US 2014/0199291 A9    Jul. 17, 2014

Related U.S. Application Data

(60) Provisional application No. 60/993,769, filed on Sep. 14, 2007.

(51) Int. Cl.
*A61K 39/00* (2006.01)
*A61K 31/4709* (2006.01)
*A61K 31/47* (2006.01)
(Continued)

(52) U.S. Cl.
CPC .......... *A61K 31/4709* (2013.01); *A61K 31/196* (2013.01); *A61K 31/352* (2013.01); *A61K 31/437* (2013.01); *A61K 31/44* (2013.01); *A61K 31/47* (2013.01); *A61K 31/554* (2013.01); *A61K 31/573* (2013.01); *A61K 31/575* (2013.01); *A61K 31/58* (2013.01); *A61K 31/69* (2013.01); *A61K 31/7048* (2013.01);
(Continued)

(58) Field of Classification Search
None
See application file for complete search history.

(56) References Cited

U.S. PATENT DOCUMENTS 5,834,505 A    11/1998    Peters
6,294,570 B1    9/2001    Krause
(Continued)

FOREIGN PATENT DOCUMENTS

WO        WO 00/44359        8/2000

OTHER PUBLICATIONS

Turnidge, "Fusidic acid pharmacology, pharmacokinectics and pharmacodynamics," Int. J. Antimicrob Agents, Suppl 2: pp. 523-534 (1999).*

(Continued)

*Primary Examiner* — Zachariah Lucas
*Assistant Examiner* — M. Franco Salvoza
(74) *Attorney, Agent, or Firm* — Wolf, Greenfield & Sacks, P.C.

(57) ABSTRACT

The invention relates to compositions, methods, and kits for treating subjects infected by or at risk of infection with a DNA virus (e.g., a JC Virus or a BK virus). Aspects of the invention are useful to prevent or treat DNA virus associated conditions (e.g., PML) in subjects that are immunocompromised. Compositions are provided that inhibit intracellular replication of DNA viruses.

8 Claims, 16 Drawing Sheets

(51) Int. Cl.

| | |
|---|---|
| A61K 45/06 | (2006.01) |
| A61K 31/196 | (2006.01) |
| A61K 31/352 | (2006.01) |
| A61K 31/437 | (2006.01) |
| A61K 31/44 | (2006.01) |
| A61K 31/554 | (2006.01) |
| A61K 31/573 | (2006.01) |
| A61K 31/575 | (2006.01) |
| A61K 31/58 | (2006.01) |
| A61K 31/69 | (2006.01) |
| A61K 31/7048 | (2006.01) |
| A61K 38/12 | (2006.01) |
| A61K 39/395 | (2006.01) |
| A61M 1/38 | (2006.01) |

(52) U.S. Cl.
CPC ............ *A61K 38/12* (2013.01); *A61K 39/3955* (2013.01); *A61K 45/06* (2013.01); *A61M 1/38* (2013.01)

(56) References Cited

U.S. PATENT DOCUMENTS

| | | | | |
|---|---|---|---|---|
| 6,462,182 | B1 | 10/2002 | Tuinman | |
| 6,685,928 | B2 | 2/2004 | Uhrich | |
| 2003/0072793 | A1* | 4/2003 | Frey et al. | 424/449 |
| 2005/0053660 | A1* | 3/2005 | Beckert et al. | 424/470 |
| 2006/0286574 | A1* | 12/2006 | Romesberg et al. | 435/6 |
| 2007/0129282 | A1* | 6/2007 | Ahlem et al. | 514/2 |
| 2007/0231319 | A1* | 10/2007 | Yednock | 424/131.1 |
| 2008/0161324 | A1* | 7/2008 | Johansen et al. | 514/255.03 |

OTHER PUBLICATIONS

Dobie et al., "Fusidic acid resistance in *Staphylococcus aureus*," Arch Dis Child 89: pp. 74-77 (2004).*

Collignon et al., "Fusidic acid in vitro activity," International Journal of Antimicrobial Agents 12: S45-S58 (1999).*

Maehlen et al., "Lack of Activity of Fusidic Acid against Human Immunodeficiency Virus in Monocytes," Antimicrobial Agents and Chemotherapy, vol. 33. No. 5: 680-683 (1989).*

Dupasquier et al., "JCV-specific cellular immune response correlates with a favorable clinical outcome in HIV-infected individuals with progressive multifocal leukoencephalopathy," Journal of NeuroVirology 7: 318:322 (2001).*

Faber et al., "Inhibition of HIV Replication in vitro by Fusidic Acid," The Lancet ii: 827-828 (1987)).*

Famularo et al., "In Vivo and in Vitro Efficacy of Fusidic Acid in HIV infection," Ann NY Acad Sci 685: 341-3 (1993).*

Abdelrahim et al., "Tolfenamic Acid and Pancreatic Cancer Growth, Angiogenesis, and Sp Protein Degradation," Journal of the National Cancer Institute, vol. 98, No. 12: 855-868 (2006).*

Magin et al., "Isotretinoin, depress and suicide: a review of the evidence," Br J Gen Pract 55(511): 134-138 (2005).*

Owen, et al.; "In Vitro Synergy and Enhanced Murine Brain Penetration of Saquinavir Coadministered with Mefloquine"; J. of Pharmacol. Exp. Ther. (2005); 314(3): 1202-1209.

Yousry, et al.; "Evaluation of Patients Treated with Natalizumab for Progressive Multifocal Leukoencephalopathy"; N Eng J Med (2006); 354(9): 924-933.

Langer-Gould, et al.; "Progressive Multifocal Leukoencephalopathy in a Patient Treated with Natalizumab"; N Eng J Med (2005); 353(4): 375-381.

Skinner-Adams, et al.; "Synergistic Interactions of the Antiretroviral Protease Inhibitors Saquinavir and Ritonavir with Chloroquine and Mefloquine against Plasmodium falciparum In Vitro"; Antimicrob. Agents Chemother. (2007); 51(2): 759-762.

Aksamit; "Review of Progressive Multifocal Leukoencephalopathy and Natalizumab"; Neurologist (2006); 12(6): 293-298.

* cited by examiner

A (-)-(S,R)-mefloquine $IC_{50} = 4.5 + 0.9 \mu M$ (+)-(R,S)-mefloquine $IC_{50} = 2.7 + 1.5 \mu M$ Racemate: $IC_{50} = 4.7 + 1.7 \mu M$ (S,S)-mefloquine

IC$_{50}$ = 4.6 µM (R,R)-mefloquine (2,8-Bis-trifluoromethyl-
quinolin-4-yl)-pyridin-2-yl-
methanol

IC$_{50}$ = 11.5 µM

* >20% inhibition of total cell number diclofenac $IC_{50} = 8.3\ \mu M$

Mefenamic acid $IC_{50} = 10.9\ \mu M$ flufenamic acid $IC_{50} = 11\ \mu M$

Tolfenamic acid $IC_{50} = 15\ \mu M$ flunexin $IC_{50} = 14.5\ \mu M$

MDLN Number
MFCD00153951

MDLN Number
MFCD01076457

MDLN Number
MFCD05664734

MDLN Number
MFCD002266402

**MDLN Number
MFCD00271609**

**MDLN Number
MFCD00271896**

**MDLN Number
MFCD00271937**

Fusidic acid

COMPOSITIONS AND METHODS FOR THE TREATMENT OF PROGRESSIVE MULTIFOCAL LEUKOENCEPHALOPATHY (PML)

RELATED APPLICATIONS

This application is a national stage filing under 35 U.S.C. §371 of PCT International application PCT/US2008/010734 designating the United States of America, and filed Sep. 13, 2008, which claims the benefit under 35 U.S.C. §119(e) of U.S. provisional application Ser. No. 60/993,769, filed Sep. 14, 2007, the entire contents of each of which are herein incorporated by reference.

FIELD OF THE INVENTION

The invention relates to compositions and methods for treating subjects infected with a DNA virus. In particular, aspects of the invention relate to subjects infected with JCV virus and subjects having, or at risk for developing, progressive multifocal leukoencephalopathy (PML).

BACKGROUND OF THE INVENTION

JC polyomavirus (JCV) is the causative agent of a demyelinating disease of the central nervous system, progressive multifocal leukoencephalopathy (PML). The incidence of PML can be related to a weakened immune system or treatment with immunosuppressants. Currently, there is no specific antiviral therapy that has been proven effective for treatment of PML.

SUMMARY OF THE INVENTION

Aspects of the invention relate to compositions that inhibit DNA virus activity, including viral proliferation (e.g., viral replication), mutation rate and infectivity, and the use of such compositions to treat or suppress conditions associated with DNA virus activity in subjects that are infected with a DNA virus, or the use of such compositions to lower the risk of infection with the DNA virus. In some embodiments, the invention provides one or more compositions that inhibit JCV activity. In some embodiments, the invention provides one or more compositions that inhibit BK virus (BKV) activity. Such compositions may be used to prevent DNA viral infection (e.g., JCV infection or BKV infection), to prevent an increase in DNA viral activity (e.g., active JCV infection of the brain), to prevent DNA virus proliferation (e.g., JCV proliferation or BKV proliferation) to prevent symptoms associated with viral infection (e.g., JCV or BKV infection), to treat a subject infected with a DNA virus (e.g., JCV or BKV), or treat a subject at risk of infection with a DNA virus (e.g., JCV or BKV), or to treat a subject that has developed a disease or condition associated with infection by a DNA virus (e.g., PML). Compositions of the invention also may be administered to a subject at risk of a viral infection or at risk of an increase in viral activity (e.g., viral proliferation, for example in the brain or CNS), regardless of whether the subject is actually known to have been exposed to, or infected by, the virus.

In some embodiments, one or more compositions of the invention may be administered to subjects that have a compromised immune system. It should be appreciated that a subject's immune system may be compromised due to treatment with an immunosuppressive therapeutic agent and/or due to a disease or condition that impacts the immune system. In some embodiments, one or more compositions of the invention may be administered to a subject that is at risk of PML due to a compromised immune system, regardless of whether the subject is known to be infected with JCV or known to have been exposed to JCV. Accordingly, compositions of the invention may be administered to subjects that are receiving an immunosuppressive treatment for a disease or condition. In some embodiments, compositions of the invention may be administered to multiple sclerosis (MS) patients that are being treated with one or more immunosuppressive agents (e.g., natalizumab). However, in some embodiments, compositions of the invention may be administered to subjects that have a weakened immune system caused by a disease or condition itself, rather than by an immunosuppressive treatment. For example, subjects infected with an immunocompromising pathogen (e.g., a virus such as HIV) may be treated with one or more compositions of the invention.

It should be appreciated that while the JCV status of a subject need not be known, it may be useful to know the status in some embodiments. In some embodiments, the efficacy of such treatment or therapy may be monitored by detecting and/or monitoring the presence of JCV in a subject.

In some embodiments, one or more compositions of the invention may be administered to a subject before, during, and/or after the subject receives and immunomodulatory therapy (e.g., a treatment that inhibits the immune system of the subject). Accordingly, in some embodiments one or more compounds described herein as being effective to inhibit DNA virus replication may be administered to a subject prior to initiation of an immunomodulatory therapy. For example, a therapeutic regimen of one or more compositions of the invention may be initiated prior to an immunomodulatory treatment against a disease or in preparation for a transplant in to prevent or reduce any risk of DNA virus replication or proliferation associated with the immunomodulatory treatment.

In some embodiments, one or more compositions of the invention may be administered alone or in combination with other compositions described herein or along with other therapeutic agents (e.g., one or more immunosuppressive therapeutic agents). Compositions of the invention may be provided (e.g., administered) in pharmaceutical preparations. Compositions of the invention may be provided in kits.

In some aspects, compositions of the invention may be used to develop further anti-viral treatments (e.g., as starting material for a medicinal chemistry study or as references in an in vitro assay).

In some aspects, the invention provides methods of inhibiting viral replication, the methods comprising contacting a cell comprising a DNA virus with a composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, or any combination thereof.

In some aspects, the invention provides methods of inhibiting viral replication, the methods comprising contacting a cell comprising a DNA virus with a composition comprising endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone, or any combination thereof.

In some aspects, the invention provides methods of inhibiting viral replication, the methods comprising contacting a cell comprising a DNA virus with a composition comprising mefloquine.

In some aspects, the invention provides methods of inhibiting viral replication, the methods comprising contacting a cell comprising a DNA virus with a composition comprising R*,S*-mefloquine.

In some embodiments of the methods described herein, the composition further comprises a pharmaceutically acceptable carrier.

In some embodiments of any of the methods described herein, the DNA virus is a herpes virus, pox virus, parvovirus, or polyomavirus. In some embodiments, the DNA virus is a polyomavirus. In some embodiments, the polyomavirus is JC virus. In some embodiments, the polyomavirus is BK virus.

In some embodiments of the methods described herein, a composition is contacted to a virus-infected cell in a subject. In some embodiments, the cell is a brain cell, a neuron, a kidney cell, or any other cell in a subject. Accordingly, in some embodiments a composition is administered to a subject. In some embodiments, the subject is suspected of having a viral infection (e.g., in at least one cell or tissue type). A subject suspected of having a viral infection may be a subject that has been identified as having, or known to have, a DNA virus infection (e.g., a JCV or BKV infection). In addition, or alternatively, a subject suspected of having a viral infection may be a subject that has been identified as being at risk of, or is known to be at risk of, a DNA virus infection (e.g., a JCV or BKV infection). It should be appreciated, that a subject may be identified as having an infection by directly detecting one or more viral molecules (e.g., RNA, DNA, protein, etc., or any combination thereof). However, a subject may be identified as having an infection indirectly by detecting one or more indicia of an infection (e.g., one or more symptoms, one or more serum antibodies against a viral molecule, etc., or any combination thereof). In some embodiments, one or more symptoms of a viral infection may be used to identify a subject as being at risk of a viral infection. A subject also may be identified as being at risk of a viral infection if the subject has a reduced or suppressed immune system (e.g., due to a disease, condition, or treatment, or a combination thereof as described in more detail herein). In some embodiments, the subject has been identified as having a JC virus infection in the CNS. In some embodiments, the subject has been identified as having a BK virus infection in the kidney. It should be appreciated that one or more of the compositions described herein may be administered to a subject on the basis that the subject is suspected of having a DNA virus infection. For example, a composition may be administered to a subject, because the subject had been identified as having, or known to have, or identified as being at risk of having, or known to be at risk of having, a DNA virus infection. Accordingly, in some embodiments a subject is evaluated to determine whether the subject has, or is at risk of having, a DNA virus infection (e.g., a JCV or BKV infection), and a composition described herein is administered to the subject if they are found to have, or be at risk of having, the DNA virus infection. In some embodiments, a composition described herein is not administered to a subject that is identified or known to be virus free and/or risk free.

Accordingly, in some embodiments of the invention a subject is evaluated (e.g., monitored) to determine whether the subject has a sign or symptom of, or is at risk for, a DNA virus infection or proliferation. In some embodiments, this evaluation involves determining whether the subject has a symptom of a disease or condition associated with DNA virus activation (e.g., a symptom of PML). If the subject is identified as having a sign or symptom of, or as being at risk for, a DNA virus (e.g., JCV or BKV) infection or proliferation, the subject is treated with one or more compounds or compositions of the invention. In some embodiments, a composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deamadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, or any combination thereof, is administered to the subject. In some embodiments, a composition comprising candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, or methoxyvone, or any combination thereof, is administered to the subject.

In some embodiments, the subject (e.g., a subject that has been identified and treated based on the identification) is evaluated (e.g., monitored) for one or more signs or symptoms of DNA virus infection or proliferation after receiving a compound or composition of the invention. For example, in some embodiments of the invention a subject may be evaluated to determine or confirm the reduction of at least one symptom of DNA virus (e.g., JCV or BKV) infection or proliferation. In certain embodiments, a subject may be evaluated to determine or confirm that no signs or symptoms of DNA virus (e.g., JCV or BKV) infection or proliferation have developed in the subject. In some embodiments, a subject may be evaluated to determine or confirm that any detectable signs or symptoms of DNA virus (e.g., JCV or BKV) infection or proliferation have been maintained at a stable level, or that their development has been slowed or reversed. In some embodiments, an immunomodulatory treatment or therapy may be altered (e.g., increased, decreased, substituted, or discontinued) based on the evaluation (e.g., monitoring) of the subject. In some embodiments, a treatment or therapy with one or more compounds or compositions of the invention may be altered (e.g., increased, decreased, substituted, or discontinued) based on the evaluation (e.g., monitoring) of the subject before, after, or during, an immunomodulatory therapy.

In some aspects, the invention provides methods of inhibiting viral replication in a subject, the methods comprising administering a composition to a subject suspected of having a DNA virus infection, wherein the composition comprises chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, or any combination thereof, in an amount sufficient to inhibit DNA viral replication in the subject.

In some aspects, the invention provides methods of inhibiting viral replication in a subject, the methods comprising administering a composition to a subject suspected of having a DNA virus infection, wherein the composition comprises endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone, or any combination thereof, in an amount sufficient to inhibit DNA viral replication in the subject.

In some embodiments of the methods presented herein, the DNA virus infection is a herpes virus, pox virus, parvovirus, or polyomavirus infection. In some embodiments of the methods presented herein the DNA virus infection is polyomavirus infection. In some embodiments of the methods presented herein the polyomavirus is JC virus. In some embodiments of the methods presented herein the polyomavirus is BK virus.

In some embodiments of the methods presented herein, the subject has been identified as having a JC virus infection of the CNS. In some embodiments of the methods presented herein, the subject has been identified as having a BK virus infection of the kidney.

In some embodiments of the methods presented herein the subject is identified as being at risk of a DNA virus infection. In some embodiments of the methods presented herein, the subject is undergoing, or has been undergoing, an immunomodulatory treatment. In some embodiments of the methods presented herein, the immunomodulatory treatment comprises the administration of a VLA-4 antibody. In some embodiments of the methods presented herein, the VLA-4 antibody is natalizumab.

In some aspects, the invention provides methods of reducing the risk of a DNA virus infection in a subject, the methods comprising administering to the subject a composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, or any combination thereof in an amount sufficient to inhibit DNA viral infection.

In some aspects, the invention provides methods of reducing the risk of a DNA virus infection in a subject, the methods comprising administering to the subject a composition comprising endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone or combinations thereof in an amount sufficient to inhibit DNA viral infection.

In some aspects, the invention provides methods of reducing the risk of PML, the methods comprising administering to a subject having PML, or at risk of PML, a composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, or any combination thereof in an amount sufficient to inhibit DNA viral infection.

In some aspects, the invention provides methods of reducing the risk of PML, the methods comprising administering to a subject having PML, or at risk of PML, a composition comprising endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone or combinations thereof in an amount sufficient to inhibit DNA viral infection.

In some aspects, the invention provides methods of reducing the risk of PML, the methods comprising administering to a subject having PML, or at risk of PML, a composition comprising an arylalkanoic acid.

In some embodiments of the methods presented herein, the composition is administered in a dosage sufficient to reduce the number of JCV infected cells in an in vitro assay by more than 25%, more than 40%, more than 50%, more than 75%, or more than 80%.

In some embodiments of the methods presented herein, the composition comprises a compound having an anti-JCV $IC_{50}$<20 µM and a therapeutic index $IC_{50}/TC_{50}$<0.5.

In some embodiments of the methods presented herein, the methods further comprise administering an antiviral agent.

In some embodiments of the methods presented herein, the methods further comprise performing a plasma exchange.

In some aspects, the invention provides a pharmaceutical composition and/or a kit comprising natalizumab and one or more compounds selected from the group consisting of chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, (R)-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine, 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, 4-estren-3-beta 17-beta-diol 17-acetate, 5-beta-pregnan-3-alpha 6-alpha 20-beta-triol 20-acetate, or 4-pregnen-3-beta 20-beta-diol 20-acetate, and any combination thereof.

In some aspects, the invention provides a pharmaceutical composition and/or a kit comprising natalizumab and one or more compounds selected from the group consisting of endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone and combinations thereof.

In some embodiments, the invention provides methods of treatment comprising administering to a subject having PML, or at risk of PML, a therapeutically effective amount of a pharmaceutical composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, 4-pregnen-3-beta 20-beta-diol 20-acetate, or any combination of two or more thereof.

In some embodiments, the invention provides methods of treatment comprising administering to a subject having PML, or at risk of PML, a therapeutically effective amount of a pharmaceutical composition comprising endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone or combinations thereof.

In some embodiments, the invention provides methods of treatment comprising administering to a subject having PML, or at risk of PML, a therapeutically effective amount of a pharmaceutical composition comprising mefloquine.

In some embodiments, the invention provides methods of treatment comprising administering to a subject having PML, or at risk of PML, a therapeutically effective amount of a pharmaceutical composition comprising R,S-mefloquine.

In some embodiments, the invention provides methods of treatment comprising administering to a subject having PML, or at risk of PML, a therapeutically effective amount of a pharmaceutical composition comprising a compound with the same mode of action as endosulfan, candesartan cilextil, mefenamic acid, fusidic acid, tolfenamic acid, mefloquine, isotretinon, diclofenac sodium, diltiazem hydrochloride, miconazole nitrate, flunixin meglumine, propanil, dehydroabietamide, diffractic acid, harmane, xanthone, methoxyvone or any combination thereof.

In some embodiments, the invention provides methods of treatment comprising administering to a subject having PML, or at risk of PML, a therapeutically effective amount of a pharmaceutical composition comprising a compound comprising an adenosine, guanine, estren, or pregnan component.

In some embodiments, the invention provides methods of treatment comprising administering to a subject having PML, or at risk of PML, a therapeutically effective amount of a pharmaceutical composition comprising a compound comprising an arylalkanoic acid.

In some embodiments, the invention provides methods of treating a subject infected with a DNA virus, or suspected of being infected with a DNA virus, the method comprising administering to a subject a therapeutically effective amount of a pharmaceutical composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, 4-pregnen-3-beta 20-beta-diol 20-acetate, or any combination of two or more thereof.

In some embodiments, the invention provides methods of treatment for a subject infected with a DNA virus, or suspected of being infected with a DNA virus, wherein the DNA virus is selected from the group consisting of herpes virus, pox virus, parvovirus and polyomavirus. In some embodiments, the invention provides methods of treatment for a subject infected with JC virus, or suspected of being infected with JC virus. In some embodiments, the invention provides methods of treatment for a subject infected with BK virus, or suspected of being infected with BK virus. In some embodiments, the invention provides methods of treatment for a subject infected with a JC virus, wherein JC virus infection is characterized by the presence of JC virus in the central nervous system (CNS). In some embodiments, the invention provides methods of treatment for a subject infected with a BK virus, wherein BK virus infection is characterized by the presence of BK virus in the kidney.

In some embodiments, the invention provides methods of preventing or suppressing PML, the method comprising administering to a subject a therapeutically effective amount of a pharmaceutical composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, 4-pregnen-3-beta 20-beta-diol 20-acetate, or any combination of two or more thereof.

In some embodiments, the invention provides methods of treatment of a subject having PML, or suspected of having PML, the method comprising administering to a subject a therapeutically effective amount of a pharmaceutical composition comprising a compound in a dosage sufficient to reduce the number of JCV infected cells in an in vitro assay by more than 40%.

In some embodiments, the invention provides methods of treatment of a subject having PML, or suspected of having PML, comprising administering to a subject a therapeutically effective amount of a pharmaceutical composition comprising a compound, wherein the compound has an anti-JCV $IC_{50}<20$ μM and a therapeutic index $IC_{50}/TC_{50}<0.5$.

In some embodiments, the invention provides methods of treatment for a subject infected with a DNA virus, or suspected of being infected with a DNA virus, or of a subject having PML, or suspected of having PML, wherein the subject is undergoing, or has been undergoing, immunomodulatory treatment.

In some embodiments, the invention provides methods of preventing viral infection in a person undergoing immunomodulatory treatment, the method comprising administering to a subject a therapeutically effective amount of a pharmaceutical composition comprising chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, 4-pregnen-3-beta 20-beta-diol 20-acetate, or any combination of two or more thereof.

In some embodiments, the immunomodulatory treatment comprises the administration of a VLA-4 antibody. In some embodiments, the immunomodulatory treatment comprises the administration of natalizumab.

In some embodiments, the invention provides methods of treatment for a subject infected with a DNA virus, or suspected of being infected with a DNA virus, or of a subject having PML, or suspected of having PML comprising administering one or more compounds of Table 1 and an antiviral therapeutic.

In some embodiments, the invention provides methods of treatment for a subject infected with a DNA virus, or suspected of being infected with a DNA virus, or of a subject having PML, or suspected of having PML, comprising administering one or more compounds of Table 1 and an adjuvant.

In some embodiments, the invention provides methods of treatment for a subject infected with a DNA virus, or suspected of being infected with a DNA virus, or of a subject having PML, or suspected of having PML, comprising administering multiple compounds selected from the group consisting of chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, and 4-pregnen-3-beta 20-beta-diol 20-acetate In some embodiments, the invention provides methods of treatment for a subject infected with a DNA virus, or suspected of being infected with a DNA virus, or of a subject having PML, or suspected of having PML, comprising administering one or more compounds of Table 1 and performing a plasma exchange.

In some embodiments, the invention provides a pharmaceutical composition comprising natalizumab and one or more compounds selected from the group consisting of chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate and 4-pregnen-3-beta 20-beta-diol 20-acetate.

In some embodiments, the invention provides a kit comprising natalizumab and one or more compounds selected from the group consisting of chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyxanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, and 4-pregnen-3-beta 20-beta-diol 20-acetate, and instructions for administering the compounds.

In some embodiments, the invention provides a method of inhibiting (e.g., reducing or suppressing) replication of a DNA virus in a cell comprising contacting a cell comprising a DNA virus with a compound, wherein contacting the cell with the compound results in the reduction or suppression of replication of the DNA virus, wherein the compound is selected from the group consisting of chloroacetoxyquinoline, demethylnobiletin, propanil, aminoethoxydiphenylborane, 5-nitro-2-phenylpropylaminobenzoic acid, 3beta-hydroxyisoallospirost-9(11)-ene, leoidin, picropodophyllotoxin, thiabendazole, harmane, 6,4'-dihydroxyflavone, gentiopicroside, R-angolensin, ptaeroxylin, dipyridamole, nabumetone, rosiglitazone, diltiazem hydrochloride, betamethasone, ichthynone, amcinonide, riluzole, flufenamic acid, chrysin, dictamine, piplartine, peucenin, methoxyvone, isotretinoin, chloroxylenol, tomatine, primuletin, mefenamic acid, diethylstilbestrol, chloramphenicol palmitate, methylxanthoxylin, 1-alaminol, diclofenac sodium, flunixin, meglumine, dehydroabietamide, pachyrrhizin, dicumarol, diffractic acid, acemetacin, ginkgolic acid, xanthone, fusidic acid, polymyxin b sulfate, pyrantel pamoate, 4-(3-butoxy-4-methoxybenzyl)imidazolidin-2-one, miconazole nitrate, candesartan cilextil, endosulfan, dioxybenzone, tolfenamic acid, mefloquine ([2,8-bis(trifluoromethyl)quinolin-4-yl]-piperidin-2-ylmethanol), 2-methoxyanthone, 3-hydroxy-4-(succin-2-yl)-caryolane delta-lactone, 5,7-dihydroxyflavone, avocadanofuran, benzo(a)pyrene, beta-dihydrogedunol, decahydrogambogic acid, diosmetin, niloticin, pectolinarin, totarol acetate, 8-chloroadenosine, 3-deazaadenosine, O6-cyclohexylmethylguanine, roscovitine, 4-estren-3-beta 17-beta-diol 17-acetate, 5-beta-pregnan-3-alpha 6-alpha 20-beta-triol 20-acetate, 4-pregnen-3-beta 20-beta-diol 20-acetate and any combination of two or more thereof.

In some embodiments, the invention provides a method of suppressing replication of a DNA virus in a cell, wherein the DNA virus is selected from the group consisting of herpes virus, pox virus, parvovirus, JC virus, and BK virus.

These and other aspects of the invention are described in more detail herein and illustrated by the following non-limiting figures and examples.

DETAILED DESCRIPTION OF THE INVENTION

Figure 1:
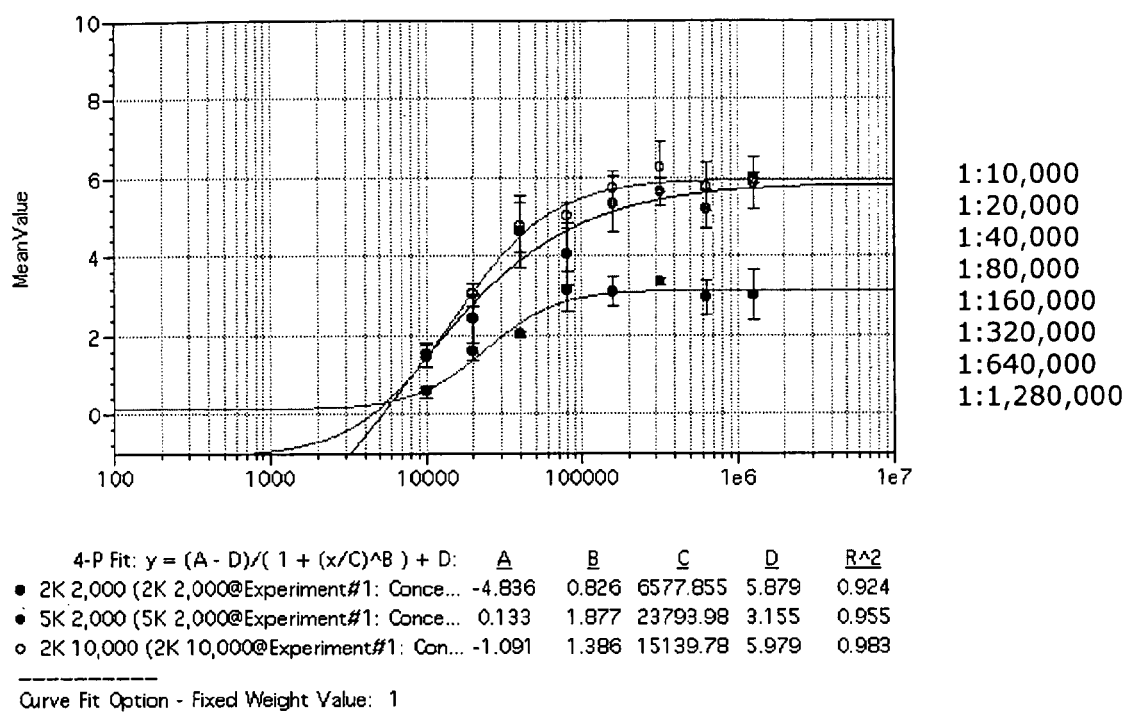
FIG. 1 illustrates a non-limiting embodiment of a decrease in the amount of inhibition with an increase in the amount of neutralizing JCV antibody added.

Aspects of the invention relate to compositions identified as having anti-viral activity and their use to prevent or treat viral infection in subjects. In particular, aspects of the invention relate to compositions found to inhibit DNA viral activity. In some embodiments, one or more compositions that inhibit JCV activity are provided and may be administered to subjects infected or at risk of infection with JCV and/or to subjects with PML, or at risk of developing PML.

Aspects of the invention are based, at least in part, on the surprising discovery that the compounds described in Table 1 reduce the percentage or number of JCV infected cells in a cell-based assay. The compounds described in Table 1 were not previously known to have anti-JCV activity or any anti-viral activity. Accordingly, one or more compounds described in Table 1 may be used as described herein.

TABLE 1

| Name | Reference | Therapeutic Indication | CAS number |
| --- | --- | --- | --- |
| CHLOROACETOXYQUINOLINE | | antifungal | 10173-02-1 |
| DEMETHYLNOBILETIN | Biochem Biophys Res Commun. 2005 Dec. 2; 337(4): 1330-6. Epub 2005 Oct. 10. | | 2174-59-6 |
| PROPANIL | U.S. Pat. No. 6,060,432 | herbicide | 709-98-8 |
| AMINOETHOXYDIPHENYLBORANE | J Neurophysiol. 2005 November; 94(5): 3069-80. Epub 2005 Jul. 13. | Ca release inhibitor, angiogensin II inhibitor | 524-95-8 |
| 5-NITRO-2-PHENYLPROPYLAMINOBENZOIC ACID [NPPB] | J Cell Physiol. 1995 January; 162(1): 15-25. | chloride channel blocker | |
| 3beta-HYDROXYISOALLOSPIROST-9(11)-ENE | J Nat Prod. 2007 July; 70(7): 1203-6. Epub 2007 Jul. 13. | | |
| LEOIDIN | | | 105350-54-7 |
| PICROPODOPHYLLOTOXIN | Biol Pharm Bull. 2007 July; 30(7): 1340-3. | antineoplastic; 10% cytotoxicity of podophyllotoxin | 477-47-4 |
| THIABENDAZOLE | U.S. Pat. No. 5,840,324 | anthelmintic | 148-79-8 |
| HARMANE | | intercalating agent, sedative | 486-84-0 |
| 6,4'-DIHYDROXYFLAVONE | | antihaemorrhagic | 79786-40-6 |
| GENTIOPICROSIDE | Yao Xue Xue Bao. 2007 May; 42(5): 566-70. | antimalarial, larvicide | |

TABLE 1-continued

| Name | Reference | Therapeutic Indication | CAS number |
|---|---|---|---|
| (R)-ANGOLENSIN | | | 4842-48-2 |
| PTAEROXYLIN | Biochem Syst Ecol. 2000 Aug. 1; 28(7): 713-716. | | 14729-11-4 |
| DIPYRIDAMOLE | U.S. Pat. No. 7,253,155 | coronary vasodilator | 58-32-2 |
| NABUMETONE | U.S. Pat. No. 6,544,556 | antiinflammatory | 42924-53-8 |
| ROSIGLITAZONE | U.S. Pat. No. 6,673,815 | antidiabetic | 122320-73-4 |
| DILTIAZEM HYDROCHLORIDE | U.S. Pat. No. 5,578,321 | Ca channel blocker, coronary vasodilator | 33286-22-5 |
| BETAMETHASONE | U.S. Pat. No. 6,878,518 | glucocorticoid, antiinflammatory | 378-44-9 |
| ICHTHYNONE | Vopr Pitan. 1995; (4): 13-6. | piscicide | 24340-62-3 |
| AMCINONIDE | U.S. Pat. No. 6,426,339 | glucocorticoid, antiinflammatory | 51022-69-6 |
| RILUZOLE | U.S. Pat. No. 6,660,757 | anticonvulsant, glutamate release inhibitor | 1744-22-5 |
| FLUFENAMIC ACID | U.S. Pat. No. 5,968,551 | antiinflammatory, analgesic | 530-78-9 |
| CHRYSIN | U.S. Pat. No. 6,607,755 | diuretic | 480-40-0 |
| DICTAMNINE | Planta Med. 2006 August; 72(10): 941-3. | | 484-29-7 |
| PIPLARTINE | Phytomedicine. 2007 September; 14(9): 605-12. Epub 2007 Mar. 30. | anti-asthma, antibronchitis | 20069-09-4 |
| PEUCENIN | Chem Pharm Bull (Tokyo). 2006 January; 54(1): 44-7. | | 578-72-3 |
| METHOXYVONE | Bioorg Med Chem. 2007 Sep. 15; 15(18): 6089-95. Epub 2007 Jun. 26. | anabolic | |
| ISOTRETINON | U.S. Pat. No. 6,936,267 | antiacne, antineoplastic | 4759-48-2 |
| CHLOROXYLENOL | U.S. Pat. No. 4,902,501 | antibacterial, topical and urinary | 88-04-0 |
| TOMATINE | U.S. Pat. No. 6,673,357 | antifungal, antibacterial, antiinflammatory agent | |
| PRIMULETIN | | | 491-78-1 |
| MEFENAMIC ACID | U.S. Pat. No. 6,645,520 | antiinflammatory, analgesic | 61-68-7 |
| DIETHYLSTILBESTROL | U.S. Pat. No. 6,040,306 | estrogen | 56-53-1 |
| CHLORAMPHENICOL PALMITATE | | antibacterial, tetratogen | 530-43-8 |
| METHYLXANTHOXYLIN | Phytother Res. 2004 July; 18(7): 542-5. | | 23121-32-6 |
| L-ALANINOL | Microbiology. 2005 July; 151(Pt 7): 2385-92. | antiproliferative | 2749-11-3 |
| DICLOFENAC SODIUM | U.S. Pat. No. 6,387,410 | antiinflammatory | 15307-79-6 |
| FLUNIXIN MEGLUMINE | U.S. Pat. No. 6,924,273 | analgesic, antiinflammatory | 42461-84-7 |
| DEHYDROABIETAMIDE | U.S. Pat. No. 4,755,523 | | |
| PACHYRRHIZIN | Trans R Soc Trop Med Hyg. 2004 August; 98(8): 451-5. | insecticide | 10091-01-7 |
| DICUMAROL | U.S. Pat. No. 5,024,998 | anticoagulant | 66-76-2 |
| DIFFRACTIC ACID | Inflamm Res. 2007 April; 56 Suppl 1: S21-2. | | |
| ACEMETACIN | U.S. Pat. No. 7,109,176 | antiinflammatory | 53164-05-9 |
| GINKGOLIC ACID | | antibacterial, antitubercular | 22910-60-7 |
| XANTHONE | U.S. Pat. No. 6,927,234 | | 90-47-1 |
| FUSIDIC ACID | U.S. Pat. No. 6,462,182 | antibacterial | 6990-06-3 |
| POLYMYXIN B SULFATE | U.S. Pat. No. 5,648,397 | antibacterial | 1405-20-5 |
| PYRANTEL PAMOATE | U.S. Pat. No. 7,144,878 | anthelmintic | 22204-24-6 |
| 4-(3-BUTOXY-4-METHOXYBENZYL)IMIDAZOLIDIN-2-ONE | Eur J Pharmacol. 2003 Mar. 28; 465(1-2): 133-9. | cAMP PDE inhibitor, inhibits cellular adhesion and superoxide & platelet aggregation | |
| MICONAZOLE NITRATE | U.S. Pat. No. 6,001,864 | antifungal (topical) | 22832-87-7, 22916-47-8 [miconazole] |
| CANDESARTAN CILEXTIL | | angiotensin 1 receptor antagonist | 170791-09-0 |
| ENDOSULFAN | U.S. Pat. No. 6,294,570 | insecticide | 115-29-7, 959-98-8 (alpha), 33213-65-9 (beta) |
| DIOXYBENZONE | U.S. Pat. No. 5,916,544 | ultraviolet screen | 131-53-3 |
| TOLFENAMIC ACID | U.S. Pat. No. 6,685,928 | antiinflammatory, analgesia | 13710-19-5 |

TABLE 1-continued

| Name | Reference | Therapeutic Indication | CAS number |
|---|---|---|---|
| MEFLOQUINE | U.S. Pat. No. 5,834,505 | antimalarial | 53230-10-7 |
| 2-METHOXYXANTHONE | | undetermined activity | 1214-20-6 |
| 3-HYDROXY-4-(SUCCIN-2-YL)-CARYOLANE delta-LACTONE | | undetermined activity | |
| 5,7-DIHYDROXYFLAVONE | | undetermined activity | 480-40-0 |
| AVOCADANOFURAN | | undetermined activity | |
| BENZO[a]PYRENE | carcinogen, binds to DNA | experimental | 192-97-2 |
| beta-DIHYDROGEDUNOL | | undetermined activity | |
| DECAHYDROGAMBOGIC ACID | | undetermined activity | |
| DIOSMETIN | | undetermined activity | 520-34-3 |
| NILOTICIN | | undetermined activity | |
| PECTOLINARIN | | undetermined activity | 28978-02-1 |
| TOTAROL ACETATE | | undetermined activity | |
| 8-CHLOROADENOSINE | | | 34408-14-5 |
| 3-DEAZAADENOSINE | | | 6736-58-9 |
| O6-CYCLOHEXYLMETHYLGUANINE | | | |
| ROSCOVITINE, (S)-ISOMER | | | |
| 4-ESTREN-3-BETA, 17-BETA-DIOL 17-ACETATE | | | |
| 5-BETA-PREGNAN-3-ALPHA, 6-ALPHA, 20-BETA-TRIOL 20-ACETATE | | | |
| 4-PREGNEN-3-BETA, 20-BETA-DIOL 20-ACETATE | | | |

In some embodiments, one or more of the compounds of Table 1 may be used (e.g., combinations of two or more, for example, 2, 3, 4, 5, 6, 7, 8, 9, 10, etc.). In some embodiments, a composition comprises multiple compounds of Table 1. In some embodiments, the treatment or prevention regimen comprises the use of multiple compositions each comprising one or more compounds of Table 1.

In some embodiments, one or more compounds related to those listed in Table 1 may be used as described herein. For example, structurally related compounds, compounds with a similar mode of action, and/or compounds that interact with one or more of the same targets (e.g., viral or cellular targets, such as receptors, intracellular pathway components or other targets) may be used to treat or prevent DNA virus (e.g., JCV) infection and or activity.

In some embodiments, the invention relates to the use of mefloquine, and compounds with a similar mode of action as mefloquine, to prevent or treat DNA viral infection or proliferation (e.g., to reduce the risk of DNA viral infection or proliferation). Mefloquine is a quinine related anti-malarial drug. Non-limiting examples of drugs with a similar mode of action are quinine, chloroquine and halofantrine. Quinines are lysosomotropic drugs that selectively accumulate inside lysosomes. The uncharged compound rapidly diffuses through the plasma and lysosomal membranes, while once charged the compound becomes trapped inside the acidic lysosomal compartment of the parasite. In some embodiments, the invention relates to the treatment or prevention of PML using lysosomotropic drugs.

In some embodiments, the invention relates to the use of (+)-(R,S)-mefloquine to prevent or treat DNA viral infection or proliferation. In some embodiments, the invention relates to the use of (−)-(S,R)-mefloquine to prevent or treat DNA viral infection or proliferation. In some embodiments, the invention relates to the use of a racemic mixture of (+)-(R,S)-mefloquine and (−)-(S,R)-mefloquine to prevent or treat DNA viral infection or proliferation. In some embodiments, the invention relates to the use of (R,R)-mefloquine to prevent or treat DNA viral infection or proliferation. In some embodiments, the invention relates to the use of (S,S)-mefloquine to prevent or treat DNA viral infection or proliferation. In some embodiments, the invention relates to the use of a mixture of (R,R)-mefloquine and (S,S)-mefloquine to prevent or treat DNA viral infection or proliferation. In some embodiments, the invention relates to the use of one or more of the following mefloquine compounds: (+)-(R,S)-mefloquine, (−)-(S,R)-mefloquine, (R,R)-mefloquine and (S,S)-mefloquine to prevent or treat DNA viral infection or proliferation.

In some embodiments, the invention relates to the use of compounds that are structurally related to mefloquine to prevent or treat DNA viral infection or proliferation. In some embodiments, compounds that are structurally related to mefloquine are compounds that comprise the 2,8-bis-trifluoromethyl-quonolin-4-yl structural group. In some embodiments, compounds that are structurally related to mefloquine are are quinolines substituted on either or both rings. In some embodiments, compounds that are structurally related to mefloquine are substituted indoles. In some embodiments, compounds that are structurally related to mefloquine are substituted 3-indoleacetic acid derivatives. In some embodiments, compounds that are structurally related to mefloquine are substituted 6-amino purine derivatives. In some embodiments, compounds that are structurally related to mefloquine are substituted 2,6-diamino purine derivatives. In some embodiments, compounds that are structurally related to mefloquine are substituted imidazopyridin-4-amines. In some embodiments, compounds that are structurally related to mefloquine are substituted imidazopyridines. In some embodiments, compounds that are structurally related to mefloquine are compounds that have a similar shape as mefloquine. In some embodiments, compounds that are structurally related to mefloquine are 3-deazaadenosine, indomethacin, mefenamic acid, 8-chloroadenosine and O6-cyclohexylmethylguanine (See FIGS. 13 and 14). In some embodiments, a compound that is structurally related to mefloquine is roscovitine. In some embodiments, a compound that is structurally related to mefloquine is S-roscovitine. In some embodiments, a compound that is structurally related to mefloquine is R-roscovitine. The antiviral effects of R-roscovitine have been described, for instance in Orba et al. (Virology 2008 Jan. 5; 370(1):173-83).

In some embodiments, the invention relates to the use of tolfenamic acid, and compounds with the same mode of action as tolfenamic acid, to prevent or treat DNA viral infection or proliferation (e.g., to reduce the risk of DNA viral infection or proliferation). Tolfenamic acid is a drug that belongs to the class of NSAIDs (Non-Steroidal Anti-Inflammatory Drugs), and acts by inhibiting isoforms of cyclooxygenase 1 and 2 (COX 1 and COX2). In some embodiments, the invention relates to the treatment or prevention of PML using NSAIDs. In some embodiments, the invention relates to the treatment or prevention of PML using NSAID arylalkanoic acids. In some embodiments, the invention relates to the treatment or prevention of PML using arylalkanoic acids.

In some embodiments, the invention relates to the use of compounds that are structurally related to tolfenamic acid to prevent or treat DNA viral infection or proliferation. In some embodiments, compounds that are structurally related to tolfenamic acid are compounds that comprise two aromatic rings linked by a nitrogen. In some embodiments, compounds that are structurally related to tolfenamic acid are arylalkanoic acids. In some embodiments, arylalkanoic acids are secondary amines in which two substituents are substituted and/or unsubstituted aryl groups. Non-limiting examples of arylalkanoic acids are dicolfenac, mefenamic acid, flufenamic acid and flunexin (See FIGS. 12 and 13).

In some embodiments, the invention relates to the use of dioxybenzone (2,2'-Dihydroxy-4-methoxybenzophenone), and compounds with the same mode of action as dioxybenzone, to prevent or treat DNA viral infection or proliferation (e.g., to reduce the risk of DNA viral infection or proliferation). In some embodiments, the invention relates to the treatment or prevention of PML using compounds that are structurally related to dioxybenzone.

In some embodiments, the invention relates to the use of endosulfan, and compounds with the same mode of action as endosulfan, to prevent or treat DNA viral infection or proliferation (e.g., to reduce the risk of DNA viral infection or proliferation). Endosulfan can act as a protein channel agonist. In some embodiments, the invention relates to the treatment or prevention of PML using protein channel antagonists. In some embodiments, the invention relates to the treatment or prevention of PML using compounds that are structurally related to endosulfan.

In some embodiments, the invention relates to the use of candesartan cilextil, and compounds with the same mode of action as candesartan cilextil, to prevent or treat DNA viral infection or proliferation (e.g., to reduce the risk of DNA viral infection or proliferation). Candesartan cilextil can act as an angiotensin II antagonist. In some embodiments, the invention relates to the treatment or prevention of PML using angiotensin II antagonists. In some embodiments, the invention relates to the treatment or prevention of PML using compounds that are structurally related to candesartan cilextil.

In some embodiments, the invention relates to the use of fusidic acid, and compounds with the same mode of action as fusidic acid, to prevent or treat DNA viral infection or proliferation (e.g., to reduce the risk of DNA viral infection or proliferation). In some embodiments, the invention relates to the treatment or prevention of PML using antibiotics. In some embodiments, the invention relates to the treatment or prevention of PML using compound that interfere with bacterial protein synthesis. In some embodiments, the invention relates to the treatment or prevention of PML using compounds that are structurally related to fusidic acid. In some embodiments, compounds that are structurally related to fusidic acid are steroid derivatives. In some embodiments, compounds that are structurally related to fusidic acid are 4-estren-3-beta 17 beta-diol 17-acetate, 5-beta-pregnan-3-alpha 6-alpha 20-beta-triol 20-acetate and 4-pregen-3-beta 20-beta-diol 20-acetate.

In some embodiments, the invention relates to the treatment or prevention of PML using compounds that are structurally related to candesartan cilextil.

In some embodiments, the invention relates to the use of mefenamic acid, and compounds with the same mode of action as mefenamic acid, to prevent or treat DNA viral infection or proliferation (e.g., to reduce the risk of DNA viral infection or proliferation). Mefenamic acid is a drug that belong to a class of NSAIDs. In some embodiments, the invention relates to the treatment or prevention of PML using NSAIDs.

In one aspect, the invention provides methods of treatment of a subject infected with a DNA virus. In some embodiments, the DNA virus is a JC virus. In some embodiments, the DNA virus is a BK virus. In some embodiments, the invention provides methods of treatment or prevention for subjects having, or at risk of developing, progressive multifocal leukoencephalopathy (PML).

It should be appreciated that the inhibitory compounds or compositions described herein may be used to reduce or suppress DNA replication of DNA viruses (e.g., JC virus, BK virus, or any other DNA virus).

The human genome is exposed to and may acquire many viruses during the lifetime of an individual. One group of viruses the genome is exposed to are DNA viruses. DNA viruses include papova viruses and herpes viruses. Examples of papova viruses include, but are not limited to SV40, human or bovine papilloma virus (HPV or BPV), polyoma virus and human SV40-like viruses such as BK (BKV) or JC (JCV). Examples of herpes viruses include, but are not limited to herpes simplex virus (HSV), cytomegalovirus (CMV), Epstein-Barr virus (EBV), varicella or chickenpox virus, herpes zoster or shingles virus. Exposure to a DNA virus is often asymptomatic and a subject may not be aware that it has been exposed to a DNA virus. Exposure to DNA viruses often leads to integration of the DNA virus in the human genome. In a subject with a healthy immune system, the immune system will generally suppress the proliferation of the virus. However, in immuno-compromised subjects or in subjects undergoing immune treatment, DNA viruses may be expressed and proliferate resulting in the development of disease.

In one aspect, the current invention provides methods of treating subjects infected with the JC polyomavirus (JCV). Primary infection with JCV can occur asymptomatically during childhood (Padgett et al., 1971 *Lancet.*, 1257-1260). JCV is then disseminated throughout the body, probably through viraemia (Ikegaya et al., 2004, *Archives of Virology* 149, 1215-1220). It is thought that JCV persists mostly in brain and renal tissue. While infection by JCV is asymptomatic in most subjects, infection can result in serious conditions (such as PML) and even death. PML is an extremely debilitating demyelination disease of the central nervous system. PML is generally characterized by neurological deficits that progress rapidly, typically without signs of intracranial pressure, including hemiparesis, cognitive disturbance, visual field deficits, ataxia, aphasia, cranial nerve deficits and sensory deficits. Patients who have PML typically deteriorate rapidly and death commonly occurs within 6 months of diagnosis (Demeter L M. J C, B K, and other polyomaviruses; progressive multifocal leukoencephalopathy. In Mandell G L, Bennett J E, Dolin, eds. Mandell, *Douglas and Bennett's Principles and Practice of Infectious Diseases,* 4th edition, Vol. 2. New York, N.Y.: Churchill Livingstone; 1995: 1400-1406). Subjects most susceptible to PML are subjects that are immuno-compromised (e.g., AIDS patients) or subjects undergoing treatment with immunosuppressants (for instance after organ transplant or to treat an inflammation related condition such as multiple sclerosis or rheumatoid arthritis).

PML has been reported to be associated with certain JCV variants that have acquired sequence variations relative to a "wild type" JCV sequence (Zheng et al., 2004, *Microbes Infect.,* 6, 596-603). A "wild type" JCV sequence is used herein to refer to the sequence of any of the archetypes of JCV found in healthy subjects not having PML, and/or not being at risk for PML. In some embodiments, a consensus "wild type" reference sequence may be an average of sequences found in a group of healthy subjects. Interestingly, in subjects having PML, a JCV with a number of sequence variations was isolated from the brain, while a wild type variant was isolated from the urine of the same individual (Yogo et al., 2004, *Rev Med Virol* 14, 179-191). Accordingly, a subject may be infected with several different versions of JCV concurrently. In some embodiments of the present invention, a subject infected with a JCV variant associated with PML is a subject at risk for developing PML.

In one aspect, the current invention provides methods of treating subjects infected with the BK virus. Infection with BK virus is thought to be widespread but mostly asymptomatic. The lung, eye, liver, brain and kidney are sites of BK virus-associated disease. Infection in the kidney can lead to hemorrhage, non-hemorrhagic cystitis, ureteric stenosis and nephritis. Infection in the CNS has been associated with encephalitis and Guillian-Barre syndrome. An overview of diseases associated with BK virus can be found for instance in Reploeg et al. (Clinical Infectious Diseases 2001; 33: 191-202), the contents of which are incorporated herein by reference. In some embodiments, the current invention provides methods of treating subjects at risk for infection by BK virus. Subjects that are immuno-compromised or receiving immunosuppressive agents are at an increased risk for BK virus infection resulting in pathogenesis. Pathogenic BK virus infection can be especially problematic in patients undergoing a kidney transplant, which is often accompanied with the use of immunosuppressive agents.

It should be appreciated that an immunosuppressive agent may increase the susceptibility of a subject to the progression or flare up of a latent microbial infection or to the contraction of a new microbial infection. In some embodiments, the microbial infection is infection by a DNA virus. In some embodiments, the microbial infection is infection by JCV, which causes PML. In some embodiments, the microbial infection is infection by BK virus. In some embodiments, subjects that are immuno-compromised (e.g., AIDS patients) or subjects undergoing treatment with immunosuppressants are subjects art risk for PML. Subjects at risk for PML include subjects that may receive or have received treatment with one or more immunosuppressive agents (also called immunosuppressants). In some cases, the immunosuppressive agent is administered to the subject for treatment of a disease or condition, including one or more of the following non-limiting examples: cancer, organ transplant, tissue transplant, an inflammatory condition or disease, multiple sclerosis (MS), arthritis, or any combination thereof. In some embodiments, the immunosuppressive agent is an anti-VLA-4 antibody (e.g., natalizumab). In some cases, an at-risk subject tests positive for the presence of a JCV nucleic acid or a JCV polypeptide. In other cases, the at-risk subject does not test positive for the presence of a JCV nucleic acid or a JCV polypeptide.

Currently, there is no specific antiviral therapy that has been proven effective for treatment of JCV infection, and current treatment of immuno-compromised subjects infected with JCV, or at risk for JCV infection, is primarily focused on improving the function of the immune system in general. Similarly, in subjects infected with JCV or at risk for JCV infection that are receiving immuno-therapy, current treatment methods of the JCV infection are limited to termination or decrease in dose of the immuno-therapy. Therapies currently used to treat PML rely on enhancement of the immune response, e.g., HAART (Highly Active Anti-Retroviral Therapy) in HIV positive patients (e.g., Marzocchetti et al., 2005, *J Clin Microbiology* 434: 4175-4177) or decrease in the amount of immunosuppressive drugs in subjects receiving those drugs (e.g., transplant patients). Methods of treatment of JCV include, but are not limited to, IFN-alpha, cytarabine, and cidofovir. 5HT2a blockers may also be used as a treatment and are currently under study.

In some embodiments, a subject receiving an immunosuppressive agent may be treated with compositions comprising one or more of the compounds of Table 1. In some embodiments, the treatment is prophylactic, e.g., the subject receiving immunosuppressants may be treated with compositions comprising one or more compounds of Table 1, even if the subject has not been shown to be infected with a DNA virus, including JCV or BKV, and does not show any symptoms associated with PML.

In some embodiments, a subject may be treated by combining immunosuppressive treatment with treatment against DNA virus infection or the development of diseases associated with DNA virus infection, including PML. In one aspect, the invention comprises methods of treatment comprising the administration of one or more compounds of Table 1 and an immunosuppressant. In one aspect, the invention comprises methods of treatment comprising the administration of one or more compounds of Table 1 and natalizumab. In one aspect, the invention comprises methods of treatment comprising the administration of a composition comprising one or more compounds of Table 1 and an anti-VLA-4 antibody (e.g., natalizumab).

In some embodiments, administration of one or more compounds of Table 1 may be combined with methods to remove or partially remove an immunosuppressant from the bloodstream of a subject. In some embodiments, the immunosuppressant may be removed from the bloodstream prior to administration of one or more compounds of Table 1. In some embodiments, the one or more compounds of Table 1 may be combined with a compound that can bind to an immunosuppressant resulting in an increased clearance of the immunosuppressant from the bloodstream. In some embodiments, the method of removal or partial removal of the immunosuppressant from the bloodstream of a subject is plasma exchange (PLEX). In plasma exchange blood is taken from the body and plasma containing the immunosuppressant is removed from the blood by a cell separator. Blood can be removed from the body in batches or it can be removed in a continuous flow mode, with the latter allowing for the reintroduction of the processed blood into the body. The removed plasma comprising the immunosuppressants will be discarded and the patient will receive donor plasma or saline with added proteins in return. In some embodiments, multiple rounds of plasma exchange may be needed to remove the immunosuppressant from the blood or to lower the level of the immunosuppressant in the blood to an acceptable level. Methods of plasma exchange are well known in the art and are described for instance in U.S. Pat. No. 6,960,178.

The term "immunomodulatory" treatment or therapy refers to the administration of one or more compounds that modulate (e.g., upregulate or downregulate) one or more aspects of a subject's immune system. In some embodiments, an immunomodulatory treatment or therapy involves the administration of one or more immunosuppressive agents to a subject. In some embodiments, an immunomodulatory treatment or therapy downregulates the immune system of a subject. Accordingly, in some embodiments, an immunomodulatory therapy is an immunosuppressive therapy. In some embodiments, an immunomodulatory treatment or therapy downregulates the immune system of a subject. It should be appreciated that an immunomodulatory treatment or therapy (e.g., an immunosuppressive treatment or therapy) as used herein also may be referred to as an immunotherapy in the context of methods described herein.

The term "immunosuppressive agent" as used herein refers to substances that act to suppress or mask the immune system of a subject being treated herein. Immunosuppressive agents may be substances that suppress cytokine production, downregulate or suppress self-antigen expression, or mask the MHC antigens. Examples of such agents include 2-amino-6-aryl-5-substituted pyrimidines (see e.g., U.S. Pat. No. 4,665,077); nonsteroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antagonists including anti-interferon-alpha, -beta, or -gamma antibodies, anti-tumor necrosis factor-alpha antibodies (infliximab or adalimumab), anti-TNF-alpha immunoahesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-CD20 antibodies (e.g., rituximab, for example available under the trademark RITUXAN); anti-L3T4 antibodies; anti-VLA-4 antibodies (e.g., natalizumab); heterologous anti-lymphocyte globulin; pan-T antibodies, for example anti-CD3 or anti-CD4/CD4a antibodies; soluble peptide containing a LFA-3 binding domain (WO 90/08187 published Jul. 26, 1990); streptokinase; TGF-beta; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al., Science, 251: 430432 (1991); WO 90/11294; laneway, Nature, 341: 482 (1989); and WO 91/01133); and T cell receptor antibodies (EP 340,109) such as T10B9. However, subjects receiving other immunosuppressive agents are also encompassed by the invention.

Accordingly, immunosuppressive agents may be drugs that inhibit or prevent certain aspects of the immune system. Immunosuppressive agents may be drugs that are used in immunomodulatory (e.g., immunosuppressive) therapy, for example, to prevent the rejection of transplanted organs or tissues (e.g., bone marrow, heart, kidney, liver), to treat autoimmune diseases or diseases that are suspected of being associated with an autoimmune reaction (e.g., rheumatoid arthritis, multiple sclerosis, myasthenia gravis, systemic lupus erythematosus, an inflammatory bowel disease or syndrome, including, for example, Crohn's disease, ulcerative colitis, and pemphigus), or to treat a non-autoimmune inflammatory disease or condition (e.g., for term allergic asthma control).

Immunosuppressive agents may be classified into five general categories: glucocorticoids, cytostatics, antibodies, drugs acting on immunophilins, and other drugs. Glucocorticoids may include drugs that suppress cell-mediated immunity (e.g., by inhibiting IL-1, IL-2, IL-3, IL-4, IL-5, IL-6, IL-8, and/or TNF-γ. However, glucocorticoids also may suppress humoral immunity. Cytostatics may include drugs that inhibit cell division (e.g., agents that inhibit T cell and/or B cell proliferation). In some embodiments, cytostatics may be alkylating agents such as nitrogen mustards (e.g., cyclophosphamide), nitrosureas, platinum compounds, and others. In certain embodiments, immunosuppressive agents may be antimetabolites such as folic acid analogs (e.g., methotrexate), purine analogs (e.g., azathiprine, mercaptopurine), pyrimidine analogs, or protein synthesis inhibitors. An immunosuppressive agent also may be a cytotoxic antibiotic such as dactinomycin, an anthracycline, mytomicin C, bleomycin, or mithramycin. Cytostatic antibodies may be polyclonal or monoclonal antibodies that inhibit one or more aspects of the immune system (e.g., that inhibit T lymphocytes). Non-limiting examples of immunosuppressive polyclonal preparations include Atgam®, obtained from horse serum, and Thymoglobuline®, obtained from rabbit serum. In some embodiments, monoclonal antibodies may be IL-2 receptor (CD25) and/or CD3 directed antibodies. Non-limiting examples of immunosuppressive monoclonal antibodies include T-cell receptor directed antibodies (e.g., murorab, an anti-CD3 antibody), and/or IL-2 receptor directed antibodies (e.g., basiliximab (Simulect®) and daclizumab (Zenapax®). Cytostatic drugs acting on immunophilins may include cyclosporin, tacrolimus (e.g., Prograf), and/or sirolimus (e.g., Rapamune, or Rapamycin). Other cytostatic drugs may include interferons, opioids, TNF binding proteins (e.g., infliximab (e.g., Remicade), etanercept (e.g., Embrel), or adalimumab (e.g., Humira)), myophenolate, and/or small biological agents (e.g., FTY720, or myriocin).

Immunosuppressive agents that may be used to reduce the risk of transplant rejection include, but are not limited to: calcineurin inhibitors (e.g., Cyclosporin or Tacrolimus), mTOR inhibitors (e.g., Sirolimus or Everolimus), anti-proliferatives (e.g., Azathioprine, Mycophenolic acid), corticosteroids (e.g., prednisolone or hydrocortisone), and/or antibodies (e.g., monoclonal anti-IL-2Ralpha receptor antibodies such a basiliximab or daclizumab or polyclonal anti-T-cell antibodies such as anti-thymocyte globulin (ATG) or anti-lymphocyte globulin (ALG)).

In some embodiments, the immunosuppressant is a VLA-4 binding antibody like natalizumab (also known as TYSA-BRI®). In some embodiments, a VLA-4 binding antibody is an IgG antibody (e.g., an IgG4 antibody). In some embodiments, a VLA-4 binding antibody is a polyclonal or monoclonal antibody. In some embodiments, a VLA-4 binding antibody is a humanized version of a murine antibody. Natalizumab and related VLA-4 binding antibodies are described, e.g., in U.S. Pat. No. 5,840,299. mAb 21.6 and HP1/2 are exemplary murine monoclonal antibodies that bind VLA-4. Natalizumab is a humanized version of murine mAb 21.6 (see, e.g., U.S. Pat. No. 5,840,299). A humanized version of HP1/2 has also been described (see, e.g., U.S. Pat. No. 6,602,503). Several additional VLA-4 binding monoclonal antibodies, such as HP2/1, HP2/4, L25 and P4C2, are described (e.g., in U.S. Pat. No. 6,602,503; Sanchez-Madrid et al., 1986 Eur. J. Immunol., 16:1343-1349; Hemler et al., 1987 J. Biol. Chem. 2:11478-11485; Issekutz and Wykretowicz, 1991, J. Immunol., 147: 109 (TA-2 mab); Pulido et al., 1991 J. Biol. Chem., 266(16):10241-10245; and U.S. Pat. No. 5,888,507). Many useful VLA-4 binding antibodies interact with VLA-4 on cells, e.g., lymphocytes, but do not cause cell aggregation. However, other anti-VLA-4 binding antibodies have been observed to cause such aggregation. HP1/2 does not cause cell aggregation. The HP1/2 MAb (Sanchez-Madrid et al., 1986 Eur. J. Immunol., 16:1343-1349) has an extremely high potency, blocks VLA-4 interaction with both VCAM1 and fibronectin, and has the specificity for epitope B on VLA-4. This antibody and other B epitope-specific antibodies (such as B1 or B2 epitope binding antibodies; Pulido et al., 1991 J. Biol. Chem., 266(16):10241-10245) represent one class of useful VLA-4 binding antibodies.

An exemplary VLA-4 binding antibody has one or more CDRs, e.g., all three HC CDRs and/or all three LC CDRs of a particular antibody disclosed herein, or CDRs that are, in sum, at least 80, 85, 90, 92, 94, 95, 96, 97, 98, or 99% identical to natalizumab. In one embodiment, the H1 and H2 hypervariable loops have the same canonical structure as those of natalizumab. In some embodiments, the L1 and L2 hypervariable loops have the same canonical structure as natalizumab. In some embodiments, the amino acid sequence of the HC and/or LC variable domain sequence is at least 70, 80, 85, 90, 92, 95, 97, 98, 99, or 100% identical to the amino acid sequence of the HC and/or LC variable domain of natalizumab. The amino acid sequence of the HC and/or LC variable domain sequence can differ by at least one amino acid, but no more than ten, eight, six, five, four, three, or two amino acids from the corresponding sequence of, natalizumab. For example, the differences may be primarily or entirely in the framework regions. The amino acid sequences of the HC and LC variable domain sequences can be encoded by a sequence that hybridizes under high stringency conditions to a nucleic acid sequence described herein or one that encodes a variable domain or to a nucleic acid encoding an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of natalizumab. In some embodiments, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. The skilled artisan will realize that conservative amino acid substitutions may be made in VLA-4 binding antibodies to provide functionally equivalent variants of these antibodies. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of VLA-4 binding antibodies include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the methods of treatment or prevention comprise administering a composition comprising one or more compounds of Table 1 and one or more known or putative anti-viral compounds or compounds displaying anti-viral activity. Known or putative anti-viral compounds are compounds that suppress or inhibit viral infection, viral proliferation and/or the development of disease associated with viral infection. Anti-viral drugs can be classified as targeting one of the life cycle stages of the virus. One category of anti-viral drugs are based on interfering with viral entry. A virus binds to a specific receptor to infiltrate a target cell. Viral entry can be suppressed by blocking of the viral entry way. Anti-viral drugs that have this mode of action are anti-receptor antibodies, natural ligands of the receptor and small molecules that can bind to the receptor. A second category of antiviral drugs are compounds that suppress viral synthesis. Antiviral drugs that have this mode of action are nucleoside analogues that are similar to the DNA and RNA building blocks but deactivate the protein machinery (e.g., reverse transcriptase or DNA polymerase) used to replicate the virus. Other drugs are targeted at blocking the transcription factors of viral DNA, ribozymes, which can interfere with the production of viral DNA. Other drugs target viral RNA for destruction, including siRNAs and antisense nucleic acids against viral nucleic acid sequences. Yet another class of antiviral drugs are drugs that can interfere with the function of virus specific proteins. This class includes the HIV protease inhibitors. Antiviral drugs also include drugs directed at the release stage if the virus. This category of drugs include compounds that interfere with the proteins necessary to build the viral particles. Another class of antiviral drugs are drugs that stimulate the immune system in targeting viral infection. Drugs that fall in this class are interferons, which inhibit viral synthesis in infected cells. and antibodies that can target an infected cell for destruction by the immune system. Other anti-viral agents are described in U.S. Pat. Nos. 6,130,326, and 6,440,985, and published US patent application 20020095033. Accordingly, it should be appreciated that compounds identified herein have antiviral activity and may act through any antiviral mechanism described above. In some embodiments, compounds identified herein inhibit or suppress viral replication (e.g., viral DNA replication).

The anti-viral activity of a compound may be assayed in an in vitro cell based assay. Anti-viral activity may result from i) the interaction of a compound with the virus to prevent infection of a cell or to prevent replication, development, and/or proliferation of the virus after infection, ii) the effect of a compound on a cell to prevent infection by the virus or to prevent replication, development, and/or proliferation of the virus after infection, or iii) any other mechanism, or any combination thereof. Regardless of the mode of action, a composition of the invention may have anti-viral activity if it reduces the percentage or number of infected cells in a cell-based assay. In some embodiments, a compound (or a combination of two or more compounds) has anti-viral activity when it reduces the percentage or number of infected cells by at least 20%, at least 30%, at least 40%, at least 50%, or more (e.g., in a cell-based assay). In some embodiments, a compound has anti-viral activity when it reduces the amount of viral nucleic acids within a cell. In certain embodiments, a compound inhibits the replication of viral nucleic acids within a cell (e.g., a compound reduces the amount of viral replication by about 5%, about 10%, about 20%, about 30%, about 40%, about 50%, about 60%, about 70%, about 80%, about 90%, or higher or lower or intermediate percentages of reduction). It should be appreciated that a reduction in viral replication may be measured using a cellular assay and measuring the amount of viral DNA or the rate of viral DNA replication over time (or any other measure of viral replication) in the presence of a compound and comparing it to the viral replication in the absence of the compound or in the presence of a control compound.

It should be appreciated that certain compositions may effectively inhibit viral activity in certain cell types and not others. A composition of the invention may be useful if it is effective in certain cell types regardless of whether it is active in all cell types (or even in more than one cell type). For example, compositions of the invention may be compositions that are effective at least in one or more neural cells, for example, one or more cells of the central nervous system (e.g., glial cells, astrocytes, etc.). It should be appreciated that In some embodiments, non-cytotoxic compounds (or compounds that selectively kill infected cells) are used in compositions and methods of the invention.

In some embodiments, the methods of treatment or prevention comprise administering a composition comprising one or more compounds of Table 1 and administering a vaccine against a DNA virus. A vaccine is defined as a pharmaceutical composition that when administered to a subject in an effective amount stimulates the production of protective antibody or protective T-cell response. In some embodiments, the vaccine is protein vaccine comprising one or more polypeptide sequences encoded by a DNA virus sequence. In some embodiments, the vaccine is a nucleic acid vaccine comprising DNA viral nucleic acids. Administration regimes for vaccines are known to a person of ordinary skill in the art. In some embodiments, ranges of amounts of polypeptide vaccines for prophylaxis of DNA viral infection are from 0.01 to 100 microgram/dose, for example 0.1 to 50 microgram/dose. Several doses may be needed per subject in order to achieve a sufficient immune response and subsequent protection against DNA viral infection (e.g., "immunizing" a subject). The term "immunizing" refers to the ability of a substance to cause a humoral and/or cellular response in a subject, whether alone or when linked to a carrier, in the presence or absence of an adjuvant, and also refers to an immune response that blocks the infectivity, either partially or fully, of an infectious agent.

In some embodiments, the methods of treatment or prevention comprise administering one or more compounds of Table 1 and administering an antibody against a DNA virus. In some embodiment the methods of treatment or prevention comprise administering one or more compounds of Table 1 and administering an antibody against JCV. Antibodies may be used in therapy to treat subjects with PML and/or to prevent infection by and/or suppress the activity of JCV and other DNA viruses. Suitable antibodies or fragments thereof may be selected for the ability to bind one or more polypeptides encoded by a DNA virus, including JCV. The antibody or antigen-binding fragment thereof may be an IgG1, IgG2, IgG3, IgG4, IgM, IgA1, IgA2, IgAsec, IgD, IgE or may have an immunoglobulin constant and/or variable domain of an IgG1, IgG2, IgG3, IgG4, IgM, IgA1, IgA2, IgAsec, IgD or IgE. In some embodiments, the antibody is a bispecific or multispecific antibody. In some embodiments, the antibody is a recombinant antibody, a polyclonal antibody, a monoclonal antibody, a humanized antibody or a chimeric antibody, or a mixture of these. In some embodiments, the antibody is a human antibody, e.g., a human monoclonal antibody, polyclonal antibody or a mixture of monoclonal and polyclonal antibodies. Antigen-binding fragments may include a Fab fragment, a $F(ab')_2$ fragment, and/or a $F_V$ fragment CDR3. Antibodies can be raised against a full length DNA virus protein or JCV protein or against polypeptides variants comprising a partial sequence of a DNA virus protein or JCV protein. Antibodies can be generated by injecting an animal, for example a rabbit or goat or mouse, with the antigen (e.g., a polypeptide of a DNA virus protein or JCV protein). In order to prepare polyclonal antibodies, fusion proteins containing a polypeptide of a DNA virus protein or JCV protein can be synthesized in bacteria by expression of corresponding DNA sequences in a suitable cloning vehicle. The fusion protein can then be purified, coupled to a carrier protein and mixed with Freund's adjuvant (to help stimulate the antigenic response by the rabbits) and injected into rabbits or other laboratory animals. Alternatively, the polypeptides can be isolated from cultured cells expressing the protein. Following booster injections at bi-weekly intervals, the rabbits or other laboratory animals are then bled and the sera isolated. The sera can be used directly or purified prior to use, e.g., by methods such as affinity chromatography, Protein A-Sepharose, Antigen Sepharose, Anti-mouse-Ig-Sepharose. The sera can then be used to probe protein extracts run on a polyacrylamide gel to identify the DNA virus or JCV polypeptides. Alternatively, synthetic DNA virus or JCV polypeptides can be made and used to inoculate animals. To produce monoclonal DNA virus or JCV antibodies, mice are injected multiple times (see above), the mice spleens are removed and resuspended in a phosphate buffered saline (PBS). The spleen cells serve as a source of lymphocytes, some of which produce antibodies of the appropriate specificity. These are then fused with a permanently growing myeloma partner cell, and the products of the fusion are plated into a number of tissue culture wells in the presence of a selective agent such as HAT. The wells are then screened by ELISA to identify those containing cells expressing useful antibody. These are then freshly plated. After a period of growth, these wells are again screened to identify antibody-producing cells. Several cloning procedures are carried out until over 90% of the wells contain single clones which are positive for antibody production. From this procedure a stable line of clones is established to produce the antibody. A monoclonal antibody can then be purified by affinity chromatography using Protein A Sepharose, ion-exchange chromatography, as well as variations and combinations of these techniques (See e.g., U.S. Pat. No. 6,998,467). For antibodies to be used in therapy in humans, they may be 'humanized'. Humanization of antibodies involves replacing native mouse sequences with human sequences to lower the chance of an immune response once the therapeutic antibody is introduced into humans. In some embodiments, human antibodies (e.g., identified from libraries of human antibodies) may be used.

In some embodiments, the compounds that prevent or treat DNA viral infection or proliferation have an $IC_{50}<100\,\mu M$, an $IC_{50}<20\,\mu M$, an $IC_{50}<10\,\mu M$, an $IC_{50}<5\,\mu M$, or an even lower $IC_{50}$. The $IC_{50}$ (Inhibitory Concentration) is defined herein as the inhibitory concentration at which 50% of JC viral infection is inhibited. In some embodiments, the compounds that prevent or treat DNA viral infection or proliferation have a $TC_{50}>5\,\mu M$, a $TC_{50}>20\,\mu M$, a $TC_{50}>50\,\mu M$, a $TC_{50}>100\,\mu M$, or an even higher $TC_{50}$. The $TC_{50}$ (cytoToxic Concentration) is defined herein as the concentration of the inhibitor at which 50% of cells are killed. In some embodiments, the compounds that prevent or treat DNA viral infection or proliferation have an $IC_{50}/TC_{50}<5$, an $IC_{50}/TC_{50}<1$, an $IC_{50}/TC_{50}<0.5$, an $IC_{50}/TC_{50}<0.2$, an $IC_{50}/TC_{50}<0.2$ or an even lower $IC_{50}/TC_{50}$. A compound with a lower $IC_{50}/TC_{50}$ potentially has a larger potential therapeutic window, as a lower $IC_{50}/TC_{50}$ correlates to a lower $IC_{50}$ (inhibitory concentration) and a higher $TC_{50}$ (cytotoxic concentration).

In some embodiments, the compounds that prevent or treat DNA viral infection or proliferation, upon administration have a concentration in the target tissue of at least $0.5\times IC_{50}$, at least $1\times IC_{50}$, at least $2\times IC_{50}$, at least $3\times IC_{50}$, at least $10\times IC_{50}$ or higher. In some embodiments, the compounds that prevent or treat DNA viral infection or proliferation, upon administration have a concentration in the target tissue of less than $1\times TC_{50}$, less than $0.5\times TC_{50}$, less than $0.2\times TC_{50}$, less than $0.1\times TC_{50}$, less than $0.01\times TC_{50}$ or lower. In some embodiments, the compounds that prevent or treat DNA viral infection or proliferation, upon administration have an $IC_{50}/TC_{50}$ ratio in the target tissue of less than <5, an $IC_{50}/TC_{50}<1$, an $IC_{50}/TC_{50}<0.5$, an $IC_{50}/TC_{50}<0.2$, an $IC_{50}/TC_{50}<0.2$ or an even lower $IC_{50}/TC_{50}$.

Target tissue, as used herein, embraces any tissue in a subject, including but not limited to kidney, brain, liver, spleen, bone marrow, intestine, stomach. In some embodiments, the target tissue is brain tissue or CNS. In some embodiments, the target tissue is the kidney. In some embodiments, the compounds that prevent or treat DNA viral infection or proliferation have a high plasma level upon administration. In some embodiments, the compounds that prevent or treat DNA viral infection or proliferation, wherein the DNA viral infection is located in the kidney or is expected to target the kidney, have a high plasma level upon administration.

In some embodiments, infection with a DNA virus is characterized by, or has a potential to result in, infection of the brain, including the CNS and CSF. In some embodiments, one or more of the compounds of Table 1 are administered to a subject that has a DNA virus infection of the brain, is at risk for infection of the brain by a DNA virus, or has a disease associated with a DNA virus infection of the brain (e.g., PML). In some embodiments, one or more of the compounds of Table 1 are administered in conjunction with an agent that targets or facilitates delivery of the compounds across the blood brain barrier.

As used herein a "blood-brain barrier targeting agent" is a molecule or compound that is capable of crossing the blood-brain barrier and can be used to deliver a therapeutic composition of the invention across the blood-brain barrier and into the CNS. As used herein a "CNS-cell targeting agent" is a molecule or compound that delivers a composition of the invention to a region of the CNS or to, or into, a CNS cell type once the composition is inside the blood-brain barrier. It will be understood that in some embodiments of the invention, a therapeutic composition may be attached to one or more blood-brain targeting agents and may be also attached to one or more CNS cell targeting agents. Thus there may be more than one type of blood-brain barrier targeting agent and/or more than one CNS cell targeting agent attached to a carrier of the invention. In some embodiments, one or more of the compounds of Table 1 may be packaged in a carrier (e.g., a liposome) to facilitate or target delivery to the brain and/or CNS.

In some embodiments, one or more of the compounds of Table 1 may be administered directly to a tissue infected by, or suspected of being infected by, the DNA virus (e.g., JCV, BCV, or other DNA virus). In some embodiments, one or more of the compounds of Table 1 may be administered directly to the brain. In some embodiments, one or more of the compounds of Table 1 may be administered through intrathecal injection. An intrathecal injection is an injection into the spinal canal which facilitates direct delivery of a compound to the CNS and the brain, thereby circumventing the blood brain barrier. In some embodiments, intrathecal injection is performed as a method of administration of compounds that have a low oral administration.

The phrase "therapeutically-effective amount" as used herein means that amount of a compound, material, or composition comprising one or more compounds of the present invention which are effective for producing some desired therapeutic effect in a subject at a reasonable benefit/risk ratio applicable to any medical treatment. Accordingly, in some embodiments, a therapeutically effective amount prevents, minimizes, or reverses disease progression associated with infection with a DNA virus (including JCV, BCV, or other DNA virus). Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more compounds may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more compounds described herein in an amount effective to treat or prevent infection with a DNA virus. As used herein, a treatment may be prophylactic and/or therapeutic. In some embodiments, a treatment may include preventing viral infection and/or proliferation. In certain embodiments, a treatment may include inhibiting and or reducing viral infection and/or proliferation. It should be appreciated that the terms preventing and/or inhibiting may be used to refer to a partial prevention and/or inhibition (e.g., a percentage reduction, for example about 5%, about 10%, about 20%, about 30%, about 40%, about 50%, about 60%, about 70%, about 80%, about 90%, or higher or lower or intermediate percentages of reduction). However, in some embodiments, a prevention or inhibition may be complete (e.g., a 100% reduction or about a 100% reduction based on an assay).

In some embodiments, the effective amount is tissue specific. In some embodiments, the effective amount is an amount of one or more compounds of Table 1 that results in prevention or inhibition of viral activity in a specific tissue (e.g., viral proliferation in that tissue). In some embodiments, the effective amount is an amount of one or more compounds of Table 1 that results in prevention or inhibition of viral activity in the brain. In some embodiments, the effective amount is an amount of one or more compounds of Table 1 that results in about 5%, about 10%, about 20%, about 30%, about 40%, about 50%, about 60%, about 70%, about 80%, about 90%, or higher or lower or intermediate percentages of inhibition of viral activity in the brain. In some embodiments, the effective amount is an amount of one or more compounds of Table 1 that results in about 5%, about 10%, about 20%, about 30%, about 40%, about 50%, about 60%, about 70%, about 80%, about 90%, or higher or lower or intermediate percentages of reduction of viral DNA replication in a cell (e.g., as measured in a cellular assay) when compared to the percentage reduction of viral DNA replication in the absence of a compound (or when the cell is exposed to a control compound that does not have antiviral activity, e.g., saline or vehicle control). In some embodiments, the biological sample concentration of one or more compounds of Table 1 is 1 nM, 10 nM, 100 nM, 1 $\mu$M, 10 $\mu$M, 100 $\mu$M, 1 mM, 10 mM, 100 mM after administration of the one or more compounds of Table 1. In some embodiments, the biological sample concentration of one or more compounds of Table 1 is at least 10 $\mu$M after administration of the one or more compounds of Table 1. In some embodiments, the concentration of one or more compounds of Table 1 in a specific tissue is 1 nM, 10 nM, 100 nM, 1 $\mu$M, 10 $\mu$M, 100 $\mu$M, 1 mM, 10 mM, 100 mM after administration of the one or more compounds of Table 1. In some embodiments, the concentration of one or more compounds of Table 1 in a specific tissue is at least 10 $\mu$M after administration of the one or more compounds of Table 1. In some embodiments, the concentration of one or more compounds of Table 1 in the brain is 1 nM, 10 nM, 100 nM, 1 $\mu$M, 10 $\mu$M, 100 $\mu$M, 1 mM, 10 mM, 100 mM after administration of the one or more compounds of Table 1. In some embodiments, the concentration of one or more compounds of Table 1 in the brain is at least 10 $\mu$M after administration of the one or more compounds of Table 1.

Accordingly, methods of treatment of JCV infection and PML may be evaluated prior to initiating treatment with an immunosuppressive agent, during administration of an immunosuppressive agent, or assessed after an immunosuppressive agent has been administered or after treatment with immunosuppressive treatment has been terminated.

As used herein, "diagnosing" and "evaluating treatment of PML" comprises determining the presence of JCV infection. Determining the presence of JCV infection comprises the detection of JCV in one or more tissues or in fluids (which can include determining the viral load in blood and/or cerebral spinal fluid) and may include determining the sequence of JCV. Diagnostic assays include but are not limited to histopathology, immunohistochemistry, flow cytometry, cytology, patho-physiological assays, including MRI and tomography, neurological assays biochemical assays. Biochemical assays include but are not limited to variant analysis, viral genome analysis, ELISA analysis, including the use of antibodies against one or more proteins of JCV, analysis of specific proteins, platelet count, etc. Those of ordinary skill in the art will be aware of numerous diagnostic protocols and parameters that are routinely utilized in the art.

In some aspects of the invention, PML-specific diagnostic tests and methods of monitoring PML symptoms may be used in connection with monitoring and treating a subject with PML, a subject suspected of having PML, a subject at risk for PML, a subject being treated with immunosuppressants, and/or a subject currently under treatment for PML. PML diagnostic criteria may be used in the assessment of subjects being treated (e.g., to monitor efficacy of treatment) or to assist in the decision whether to treat a subject with a method or composition of the invention, including, but not limited to, whether to supplement an alternative treatment with a treatment of the invention. In some embodiments, PML diagnostic criteria may be used to assist in the decision regarding treatment of a subject with immunosuppressant, e.g., to terminate, temporarily halt, or decrease the dose of immunosuppressant treatment regimens. Symptoms of PML are neurological and include problems with hand-eye coordination, including difficulty writing and typing, as well as problems with speech, hemiparesis and nonfluent aphasia. In some cases, an MRI scan showing an increase in the extent of the high T2-weighted and low T1-weighted signal abnormalities compared to a normal reference is indicative of PML. MRI may be used to monitor changes in lesion size and progression of PML. Detection of JCV DNA by PCR in CSF is a widely used diagnostic test of PML, it has 99% specificity and 70% selectivity. Brain biopsy for detection of JCV DNA may also be performed to diagnose or assess PML. In the absence of JCV PCR+ result for CSF, a brain biopsy may be performed and JCV DNA detection in brain tissue is used as a positive diagnosis of PML. Kappos et al., *Natalizumab treatment for multiple sclerosis: recommendations for patient selection and monitoring*, Lancet Neurol., 2007 May, 6(5): 431-41, describes non-limiting examples of diagnostic and management algorithms to monitor patients (e.g., multiple sclerosis patients) that are treated with natalizumab. Patients can be monitored using a combination of clinical, MRI, and laboratory assessments. The algorithms of Kappos et al. are incorporated herein by reference in their entirety.

As used herein, methods of the invention may be carried out in subjects. A subject may be a human or a non-human animal, including, but not limited to a non-human primate, cow, horse, pig, sheep, goat, dog, cat, or rodent. In general, all embodiments described herein may be applied to human subjects where appropriate.

In some embodiments, the methods of treatment of the invention comprise administration of compositions of compounds of Table 1 in combination with candidate therapeutic compounds identified in screens for activity against DNA viral infection or PML. Candidate compounds that have activity against DNA viral infection or PML can be identified through a variety of screening methods including both in vitro screens and in in vivo screens. In vitro screens encompass both biochemical and biological assays. Biochemical assays encompass assays that can determine the binding of candidate therapeutic compounds to a specific target, e.g., a protein or other macromolecule of the DNA virus. Biological assays encompass cellular assays, which can for instance be based on the uptake of a virus in a cell, the release of a virus from a cell, infection rate, viral DNA replication (e.g., measured as a viral DNA replication rate, an amount of viral DNA in a cell, or other measure of viral DNA replication) etc., or any combination thereof. In general, the assays will have a readout (like fluorescence) which allow for the determination of the potential therapeutic efficacy of a candidate therapeutic compounds for the treatment of infection with a DNA virus or PML. In some embodiments, an assay mixture for testing a candidate agent comprises a candidate agent. A candidate agent may be an antibody, a small organic compound, or a polypeptide, and accordingly can be selected from combinatorial antibody libraries, combinatorial protein libraries, or small organic molecule libraries. Typically, pluralities of reaction mixtures are run in parallel with different agent concentrations to obtain a different response to the various concentrations. Typically, one of these concentrations serves as a negative control, e.g., at zero concentration of agent or at a concentration of agent below the limits of assay detection. Any molecule or compound can be a candidate therapeutic. Non-limiting examples of candidate therapeutics are small molecules, RNA including siRNAs, DNA including aptamers, and proteins including antibodies and antibody fragments. The invention also embraces candidate therapeutic compounds with different modes of action. Candidate agents encompass numerous chemical classes, although typically they are organic compounds, proteins or antibodies (and fragments thereof that bind antigen). In some general embodiments, the candidate agents are small organic compounds, e.g., those having a molecular weight of more than 50 yet less than about 2500, for example less than about 1000 and, in certain embodiments, less than about 500. Candidate agents comprise functional chemical groups necessary for structural interactions with polypeptides and/or nucleic acids, and may include at least an amine, carbonyl, hydroxyl, or carboxyl group, optionally at least two of the functional chemical groups or at least three of the functional chemical groups. The candidate agents can comprise cyclic carbon or heterocyclic structure and/or aromatic or polyaromatic structures substituted with one or more of the above-identified functional groups. Candidate agents also can be biomolecules such as nucleic acids, polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

In some embodiments, candidate therapeutic compounds are based on the compounds of Table 1 and comprise modified versions of the compounds of Table 1 generated through methods of medicinal chemistry known to the skilled artisan.

In another aspect, the present invention provides "pharmaceutical compositions", which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, for example from about 5% to about 70%, and in some embodiments from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (in certain embodiments, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In some embodiments, oral administrations are used.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. In certain embodiments, chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. In some embodiments, the daily dosage will range from 0.001 to 50 mg of compound per kg of body weight, for example from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for one or more compounds of the present invention to be administered alone, in general embodiments one or more compounds may be administered as a pharmaceutical formulation (composition) as described herein.

The compounds according to the invention may be formulated for administration in any convenient way for use in human or veterinary medicine, by analogy with other pharmaceuticals.

The invention also relates to a method of making a medicament for use in treating a subject, e.g., for treating or preventing a DNA virus (e.g., JCV or BKV) infection, for inhibiting a DNA virus replication or proliferation. Such medicaments can be used for prophylactic treatment of a subject at risk for or suspected of having a DNA virus infection (e.g., for treatment of a subject prior to, during, and/or after the subject receives an immunomodulatory therapy). Accordingly, one or more compounds or compositions described herein that modulate DNA virus replication or proliferation as described herein may be used for the preparation of a medicament for use in any of the methods of treatment described herein. In some embodiments, the invention provides for the use of one or more compounds or compositions of the invention (e.g., identified as inhibiting DNA virus replication) for the manufacture of a medicament or pharmaceutical for treating a mammal (e.g., a human) having one or more symptoms of, or at risk for, DNA virus infection, replication and/or proliferation (e.g., one or more symptoms of JCV or BKV activity, or one or more symptoms of another DNA virus activity). Accordingly, aspects of the invention relate to the use of one or more compounds or compositions of the invention for the preparation of a medicament for treating or preventing PML in a subject.

Accordingly, the invention also relates to one or more compounds or compositions of the invention for use as a medicament. The invention also relates to one or more of these compounds or compositions for use in methods of the invention, for example in methods of inhibiting DNA virus (e.g., JCV or BKV) replication, or of treating or preventing a disease associated with DNA virus replication or proliferation (e.g., in subjects that are about to be, are being, and/or have been treated with at least one immunomodulatory composition).

In some aspects, the invention provides kits comprising one or more compounds of Table 1 and instructions for administering the one or more compounds of Table 1. In some embodiments, the kit also comprises an immunosuppressant and instructions for administering the one or more compounds of Table 1 and the immunosuppressants. In some embodiments, the immunosuppressant is natalizumab. The components of a kit can be included in a container or package having one or more positions for each component (and each component can be separately packaged in a dry, liquid, gel, or other form).

The present invention is further illustrated by the following Examples, which in no way should be construed as further limiting.

EXAMPLES

Example 1

Detection of JCV and JCV Variants by PCR

Nucleic acids are isolated from a biological sample using established protocols (e.g., cell lysis). Because the viral DNA may have integrated in the genomic DNA or may still be present as a smaller entity, both genomic DNA and shorter DNA sequences may be isolated and subjected to PCR analysis. Upon isolation the nucleic acids are resuspended in a buffer that will facilitate PCR analysis. Buffers that facilitate PCR analysis are known to the skilled artisan and are also commercially available from manufacturers of PCR enzymes (e.g., New England Biolabs, Beverly, Mass.). Nucleotide primers are designed to result in the amplification of a JCV gene. PCR amplification is an established laboratory technique and comprises the addition of nucleotide primers, a polymerase and single nucleotides, and polymerase buffer and subjection this mixture to cycles of annealing, amplification and dissociation resulting in the amplification of a desired DNA sequence. Upon amplification, the JCV gene is separated from the residual DNA and excess single nucleotides. The amplified JCV DNA is sequenced and the resulting nucleotide sequence is translated into a peptide sequence to determine if JCV polypeptides and polypeptide variants are present in the biological sample.

Example 2

Detection of JCV and JCV Variants Using ELISA

Proteins and peptides are isolated from a biological sample using standard laboratory techniques. Both the cellular proteins and proteins of non-cellular components can be subjected to the analysis. In one assay the sample is interrogated for the presence of JCV polypeptides. The polypeptides are detected using sandwich ELISA comprising antibodies specific for JCV polypeptides. The antibodies are generated by inoculating animals (e.g., rabbits) with the JCV polypeptides of the invention resulting in polyclonal antibodies. If so desired, cells can be harvested from the inoculated animal to generate monoclonal antibodies. Methods for the generation of both polyclonal and monoclonal antibodies are routine in the art. The antibodies against JCV polypeptide and JCV polypeptide variants are immobilized on a solid surface (e.g., a 96-well plate), with one antibody type per well or surface area. The biological samples comprising the polypeptides are added to the wells and incubated with the immobilized antibodies. JCV polypeptides and JCV polypeptide variants present in the sample will bind to an antibody specific for the polypeptide. After incubation, the sample is removed and the solid surfaces are washed to remove any unbound material. As a next step, a solution containing additional antibodies specific for JCV peptides is added to the wells. This second aliquot of antibodies will create the "sandwich" (e.g., immobilized antibody:JCV polypeptide:second antibody). This second antibody can be detected using, for instance, a labeled tertiary antibody, allowing for the detection of JCV variant polypeptides. Alternatively, the secondary antibody itself may be labeled.

In a second ELISA assay, biological samples are assayed for the presence of antibodies against one or more CV polypeptides or JCV variant polypeptides. This assay can be use to determine whether a subject is currently infected with, or has previously been exposed to, JCV or a JCV variant. Even if a specific JCV variant is no longer present, antibodies against the variant may still be present in the biological sample and can be detected. In this ELISA assay JCV polypeptides are attached to a solid surface and the biological samples are incubated with these polypeptides. If antibodies specific for these polypeptides are present in the biological samples they will bind to the polypeptides. Any unbound material is again removed. The presence of bound antibody is detected using a labeled secondary antibody.

Example 3

Treatment of JCV Infection

SV40 transformed glial cells were seeded in 10% FBS media. The cells were seeded at 2000 cells per well in 75 µl of media per well. On day 2, the media was removed and replaced by 35 µl of a 1× concentrated drug aliquot combined with a 100× diluted JCV Turbo aliquot in 35 µl of 2% FBS media (JCV Turbo is a hybrid Mad-1/SVEΔ virus constructed by insertion of the regulatory region of SV40 into the regulatory region of the Mad-1 strain of JCV (Mad-1/SVE), Vacante et al., *Virology* 1989, 170: 353-361). The cells were incubated for an hour, after which another 65 uL aliquot of 1× concentrated drug in 2% FBS was added. On day 5 the cells were stained with DAPI (for total cell number) and with a mouse monoclonal antibody against SV40 VP1, which cross reacts with the JCV VP1 protein. The JCV VP1 protein is displayed on the cell surface when a cell is infected by JVC1. The ability of the drug to suppress or inhibit JCV infection is shown in Table 2. The information is tabulated as % inhibition (as measured by the number and percentage of JCV positive cells). The cytotoxocity of the drug is displayed in the third column.

In a separate experiment the $IC_{50}$ was determined. FIG. 1 shows the inhibition curve for different cell seedings. The y-axis shows the percentage inhibition depending on the concentration of neutralizing antibody added (Neutralizing antibody is a rabbit polyclonal from anti-JCV neutralizing serum).

Figure 2:
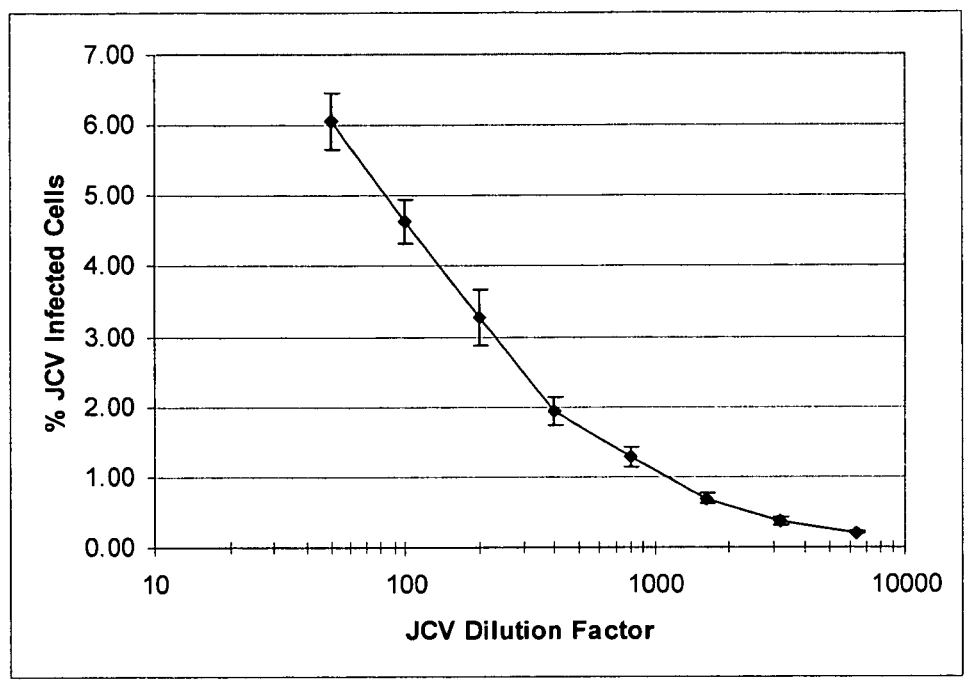
FIG. 2 illustrates a non-limiting embodiment of the correlation between infection rate and JCV virus concentration.

In a further experiment the correlation between concentration of JCV and % infection was determined. FIG. 2 shows that a JCV dilution of 1:50 results in 6% of infected cells, while a JCV dilution of 1:500 results in a 1.5% infection.

TABLE 2

Inhibition of JCV infection

| MOLENAME | Molecular Weight | % Inhibition (total #JCV+) @10 uM | sd | % Inhibition (% JCV+) @10 uM | sd | % Inhibition total Cell Number @10 uM | sd |
|---|---|---|---|---|---|---|---|
| CHLOROACETOXYQUINOLINE | 221.64276 | 38 | 0 | 20 | 2 | 20 | 2 |
| DEMETHYLNOBILETIN | 388.37384 | 38 | 0 | 20 | 2 | 20 | 2 |
| PROPANIL | 218.08202 | 12 | 14 | 21 | 0 | −12 | 17 |
| AMINOETHOXYDIPHENYLBORANE | 225.09822 | 25 | 5 | 21 | 12 | 3 | 8 |
| 5-NITRO-2-PHENYLPROPYLAMINOBENZOIC ACID [NPPB] | 300.31409 | 14 | 9 | 21 | 1 | −9 | 9 |
| 3beta-HYDROXYISOALLOSPIROST-9(11)-ENE | 414.62848 | 25 | 5 | 21 | 12 | 3 | 8 |
| LEOIDIN | 413.21021 | 14 | 9 | 21 | 1 | −9 | 9 |
| PICROPODOPHYLLOTOXIN | 414.41168 | 19 | 4 | 22 | 1 | −1 | 5 |
| THIABENDAZOLE | 201.25182 | 19 | 4 | 22 | 1 | −1 | 5 |
| HARMANE | 182.22488 | 24 | 0 | 22 | 8 | 4 | 8 |
| 6,4′-DIHYDROXYFLAVONE | 254.242 | 18 | 0 | 22 | 6 | −5 | 8 |
| GENTIOPICROSIDE | 356.32929 | 32 | 5 | 22 | 3 | 11 | 2 |
| (R)-ANGOLENSIN | 272.30063 | 18 | 0 | 22 | 6 | −5 | 8 |
| PTAEROXYLIN | 258.27374 | 32 | 5 | 22 | 3 | 11 | 2 |
| DIPYRIDAMOLE | 504.63297 | 24 | 8 | 22 | 3 | 3 | 6 |
| NABUMETONE | 228.29083 | 20 | 5 | 23 | 4 | −2 | 1 |
| ROSIGLITAZONE | 357.43323 | 22 | 3 | 23 | 3 | −1 | 8 |
| DILTIAZEM HYDROCHLORIDE | 450.98602 | 20 | 1 | 24 | 0 | −4 | 0 |
| BETAMETHASONE | 392.4675 | 34 | 0 | 24 | 4 | 14 | 4 |
| ICHTHYNONE | 408.40741 | 34 | 0 | 24 | 4 | 14 | 4 |
| AMCINONIDE | 502.5798 | 16 | 14 | 25 | 7 | −11 | 9 |

TABLE 2-continued

Inhibition of JCV infection

| MOLENAME | Molecular Weight | % Inhibition (total #JCV+) @10 uM | sd | % Inhibition (% JCV+) @10 uM | sd | % Inhibition total Cell Number @10 uM | sd |
|---|---|---|---|---|---|---|---|
| RILUZOLE | 234.2018 | 16 | 14 | 26 | 9 | −12 | 5 |
| FLUFENAMIC ACID | 281.23413 | 37 | 8 | 26 | 8 | 14 | 1 |
| CHRYSIN | 254.24199 | 18 | 5 | 26 | 8 | −12 | 5 |
| DICTAMNINE | 199.20902 | 35 | 1 | 26 | 3 | 12 | 5 |
| PIPLARTINE | 317.34152 | 21 | 11 | 27 | 2 | −7 | 11 |
| PEUCENIN | 260.28964 | 21 | 11 | 27 | 2 | −7 | 11 |
| METHOXYVONE | 266.29636 | 38 | 1 | 27 | 2 | 15 | 4 |
| ISOTRETINOIN | 300.44104 | 39 | 10 | 28 | 1 | 15 | 13 |
| CHLOROXYLENOL | 156.61157 | 36 | 2 | 29 | 10 | 10 | 9 |
| TOMATINE | 994.13745 | 40 | 8 | 29 | 15 | 12 | 7 |
| PRIMULETIN | 238.24258 | 40 | 8 | 29 | 15 | 12 | 7 |
| MEFENAMIC ACID | 241.28966 | 29 | 4 | 29 | 2 | 0 | 9 |
| DIETHYLSTILBESTROL | 268.35556 | 42 | 10 | 29 | 13 | 18 | 1 |
| CHLORAMPHENICOL PALMITATE | 505.43799 | 20 | 5 | 29 | 9 | −13 | 6 |
| METHYLXANTHOXYLIN | 210.22975 | 33 | 3 | 30 | 1 | 5 | 2 |
| L-ALANINOL | 75.110596 | 13 | 2 | 31 | 3 | −23 | 9 |
| DICLOFENAC SODIUM | 318.13409 | 44 | 2 | 31 | 1 | 18 | 4 |
| FLUNIXIN MEGLUMINE | 491.46429 | 30 | 11 | 33 | 12 | −4 | 2 |
| DEHYDROABIETAMIDE | 299.45636 | 40 | 4 | 33 | 7 | 11 | 3 |
| PACHYRRHIZIN | 336.30057 | 45 | 0 | 34 | 1 | 17 | 2 |
| DICUMAROL | 336.3006 | 36 | 13 | 35 | 11 | 3 | 4 |
| DIFFRACTIC ACID | 374.39035 | 44 | 0 | 36 | 2 | 13 | 2 |
| ACEMETACIN | 415.82962 | 32 | 7 | 38 | 3 | −8 | 6 |
| GINKGOLIC ACID | 346.51007 | 33 | 11 | 39 | 6 | −8 | 8 |
| XANTHONE | 196.20534 | 39 | 0 | 39 | 3 | 1 | 4 |
| FUSIDIC ACID | 516.7182 | 39 | 6 | 40 | 4 | −2 | 16 |
| POLYMYXIN B SULFATE | 1301.5724 | 36 | 3 | 41 | 8 | −8 | 10 |
| PYRANTEL PAMOATE | 594.68781 | 48 | 2 | 42 | 0 | 12 | 3 |
| 4-(3-BUTOXY-4-METHOXYBENZYL)IMIDAZOLIDIN-2-ONE | 278.35132 | 48 | 2 | 42 | 0 | 12 | 3 |
| MICONAZOLE NITRATE | 479.14554 | 46 | 1 | 42 | 1 | 7 | 1 |
| CANDESARTAN CILEXTIL | 610.66943 | 54 | 5 | 44 | 4 | 19 | 3 |
| ENDOSULFAN | 406.92694 | 54 | 3 | 44 | 2 | 19 | 2 |
| DIOXYBENZONE | 244.24689 | 55 | 8 | 49 | 8 | 11 | 1 |
| TOLFENAMIC ACID | 261.70752 | 61 | 2 | 53 | 0 | 18 | 5 |
| MEFLOQUINE | 378.3172 | 66 | 10 | 64 | 7 | 5 | 10 |

Example 4

Identification and Characterization of Mefloquine Efficacy Against JC Virus

In order to identify the drugs with anti-JCV activity, a commercially available collection of approved drugs and bioactive compounds were screened in in vitro JC viral infection assay. As a primary screen, inhibition of the viral infection rate was monitored in human glial cell line SVG-A (Major, Miller et al. 1985) infected with JCV strain Mad1/SVEΔ (Vacante, Traub et al. 1989). The infection rate was measured as a percent of cells expressing viral envelop protein VP1 using Cellomics ArrayScan (Pittsburgh, Pa.). Out of 2000 compounds in the SPECTRUM collection screened, 14 were identified that had inhibited the number of infected cells by >50% at the concentrations <20 μM (IC$_{50}$<20 μM). Since PML is a result of uncontrolled viral replication in the CNS, the compounds were evaluated to determine their ability to cross the blood brain barrier in sufficient concentration to be therapeutically effective. Based on the published literature, mefloquine shows CNS penetration that could be expected to achieve in vitro derived efficacious concentrations in humans (Jones, Kunsman et al. 1994; Pham, Nosten et al. 1999).

Using qPCR to quantify the number of viral copies in the culture, it also was shown that mefloquine inhibits viral DNA replication. Further experiments with mefloquine demonstrated its ability to inhibit infection by another JCV strain, Mad4 and in a different cell type, primary human astrocytes. Mefloquine is similarly effective in the inhibition of JCV infection rate even when added to the culture system 24 hrs after infection of cells with the virus, suggesting that it inhibits virus in previously infected cells. Both (+) and (−) enantiomers of mefloquine racemate were similarly potent at inhibiting JCV infection in the JCV inhibition assay.

Mefloquine hydrochloride is an antimalarial agent indicated for the treatment and prophylaxis of mild to moderate acute malaria caused by mefloquine-susceptible strains of *P. falciparum* and *P. vivax* and has a significant history of use in human population, with 11 million patients treated since 1984, when it was first registered. Although no animal model of PML or JCV infection is available to test mefloquine in vivo, in vitro results and published literature show that mefloquine is an effective anti-JCV therapy.

Materials and Methods

Compounds: The 2,000 compounds Spectrum Collection (MicroSource Discovery Inc., Groton, Conn.) consists of ~1000 Drugs defined according to the name designations as set forth in the USP Dictionary of USAN and International Drug Names (2005, US Pharmacopeia), including Food and Drug Administration (FDA) approved drugs, and other bioactive compounds and natural products. An alphabetical list of the compounds is available at "The Spectrum Collection" internet site. The compounds are supplied as 10 mM solutions in dimethyl sulfoxide (DMSO). Mefloquine was purchased from Sigma (Sigma-Aldrich, St. Louis, Mo.). Two mefloquine enantiomers were separated from a commercial mefloquine sample by Chiral Technologies (Chiral Technologies, West Chester, Pa.) using chiral HPLC on a CHIRALPAK IA column.

Cell Lines: The human glial cell line SVG-A (a gift from Walter Atwood), established by transformation of human fetal glial cells by an origin-defective SV40 mutant (Major, Miller et al. 1985), was cultured in 1× Eagle Minimal Essential Media (MEM) supplemented with 10% heat-inactivated fetal bovine serum, 4 mM L-glutamine (Mediatech, Holy Hill, Fla.). Infection was performed in 1× Eagle Minimal Essential Media (MEM) supplemented with 2% heat-inactivated fetal bovine serum, 4 mM L-glutamine (Mediatech, Inc.). Human astrocytes (ScienCell Research Laboratories, San Diego, Calif.) were isolated from fetal cerebral cortex and cultured in proprietary basal medium, supplemented with 2% fetal bovine serum, 1% astrocyte growth, and penicillin/streptomycin (ScienCell Research Laboratories). Infection of astrocytes was performed in this media.

JC Polyoma Viruses: Hybrid Mad-1/SVEDelta virus (Mad-1/SVEΔ virus) (a gift from Walter Atwood) was constructed by insertion of the regulatory region of SV40 into the regulatory region of the Mad-1 strain of JCV (Mad-1/SVE) (Vacante, Traub et al. 1989). Virus was propagated on SVG-A cells and purified as previously described (Liu, Hope et al. 1998). Briefly, SVGA cells plated at 50% confluence are infected with a 1:50 dilution of the MAD1-SVE delta strain of JC virus for 1 hour at 37° C. That concentration of virus has been shown to give a maximal infection rate of SVGA cells. Cells are cultured for 3 weeks with weekly changes of media. After 3 weeks of culture, cells are scraped from the flasks, pooled, including loose cells from prior media changes, and pelleted. The cell pellet is then resuspended in 20 ml of supernatant and disrupted in a microfluidizer (Microfluidics inc., Newton, Mass.). Deoxycholate is added to a final concentration of 0.25% and incubated at 37° C. for 30 minutes. The virus-containing cellular supernatant is then centrifuged at 10,000 RPM for 30 minutes in a SA600 rotor. The supernatant is then aliquoted and stored at −80° C. The nonarchetypal strain of JC, Mad4 (Major, Vacante et al. 1987; Frye, Trebst et al. 1997) was obtained from ATCC (Manassas, Va.).

Detection Antibodies: PAB597 (a gift from Walter Atwood), a mouse monoclonal to SV40 V antigen, cross-reacts to JCV VP1 (Atwood, Wang et al. 1995) and was used to visualize JC infection with secondary detection using an Alexa-Fluor 488-labeled goat anti-mouse secondary antibody (Molecular Probes). Cell nuclei were stained with 4',6-diamidino-2-phenylindole (DAPI) (Invitrogen, Carlsbad, Calif.). Neutralizing anti-JCV rabbit antisera was a gift from Walter Atwood (Atwood 2001).

JCV Infectivity Assay: SVG-A cells were seeded at 2,000 cells/well/0.075 ml of culture media in 96 flat-bottom well plate (Corning, N.Y.). The next day compounds were prepared in assay medium (2% heat-inactivated fetal bovine serum, 4 mM L-glutamine, 1×MEM). A master viral plate was prepared by mixing equal volumes of [2×] compound and [2×] diluted virus for the final 1× concentration of the compound and the virus. The plate containing cells was gently inverted and shaken to remove media. From the master plate, 0.035 ml compound/virus was added to designated wells. The cells were incubated with the compound/virus mixture for 60 minutes in a humidified 37° C. $CO_2$ incubator. At that time final concentration of the drug in media was added to designated wells to bring the final volume up to 0.1 ml/well. The plates were incubated for an additional three days, the cells were then washed once with 1×PBS, and fixed in 2% paraformaldehyde/1×PBS for 30 minutes at room temperature. The fixative was removed and the cells were solubilized with 0.5% Triton X100 in PBS for an additional 30 minutes. Infection by Mad-1/SVEΔ virus was visualized by staining with PAB597, a monoclonal antibody against the major capsid protein VP1, the cells were incubated with 0.05 ml of PAB597 (2 µg/ml in 1×PBS) for 60 minutes at 37° C. Following a wash step with 1×PBS, primary antibody was detected with an Alexa-Fluor 488-labeled goat anti-mouse secondary antibody at 1:100 dilution in 1×PBS, cells were counterstained with DAPI at 1 µg/ml (0.05 ml/well) for 30 minutes at 37° C. Cells were washed with 1×PBS and 0.1 ml 1×PBS was added to cells. Field images of each well were acquired and analyzed using the Cellomics ArrayScan (Thermo Scientific Inc, Waltham, Mass.) using the Target Activation software. Human astrocytes follow the same basic assay protocol with some notably exceptions. The cells are seeded at 4,000 cells/well/0.075 ml of culture media in 96 flat-bottom well plate (Corning). The culture media is used for the infection. The length of the infection is six to ten days (instead of the three days for SVG-A cells).

Real Time PCR: Taqman forward and reverse primers and MGB probes were designed for JC virus TAg using Primer Express v1.0 (Applied Biosystems, Foster City, Calif.) according to manufacture's recommendation. To create a copy number standard curve for absolute quantification, pUC19 plasmid containing JC virus genome was linearized using SmaI. Linearization was confirmed by capillary electrophoresis using an Agilent 12000 kit according to manufacturer's recommendation. Concentrations were determined by $A_{260}$ nm measurement on a nanodrop spectrophotometer. Linearized plasmid was diluted 1/10 in TE starting at 5×108/uL. Quadruplicate PCR reactions were run in a 384 well optical plate (Applied Biosystems, Foster City, Calif.). Real time reactions were cycled in a 7900HT (Applied Biosystems, Foster City, Calif.) thermal cycler under the following conditions: 50° C. for 2 minutes (uracil N-deglycosylase digest), 95° C. 10 minutes (activation of Taq thermostable polymerase), and 40 cycles of 95° C. for 15 seconds and 60° C. for 60 seconds with 900 nM forward and reverse primers, 200 nM Taqman probe, and 1× Universal master mix (Applied Biosystems, Foster City, Calif.). The fluorescence emission was collected every seven seconds for the length of the run for each reaction well. Copy number was determined for each experimental sample by comparison to the absolute JC plasmid standard curve using Sequence Detection Software (Applied Biosystems, Foster City, Calif.). The adjusted copy number was calculated by first subtracting the experimentally determined mass of JC virus DNA from the total DNA mass that was added to each 20 ul rxn well. P-values were calculated using a Student t-test. JCV copy number was quantified by comparison to a standard and normalized by the total DNA extracted from a sample. Zero copies of JC virus were detected in a non-infected negative control.

DNA Extraction and Sample Prep: DNA was extracted using to QIAamp 96 blood kit (cat#51161; Qiagen Inc., Valencia, Calif.) with optional RNase A treatment. DNA was quantitated using Quant-iT dsDNA high sensitivity assay according to manufacturer's recommendations (cat #Q33120 Molecular Probes Inc., Eugene, Oreg.). Purified DNA was stored at −20° C. until use.

Calculations: The rate of JCV infection was calculated by normalizing the number of JCV infected cells by the total number of nucleated cells as % $JCV^+$ cells=((total # $VP1^+$ cells)/(total # $DAPI^+$ cells))*100%. The % of viral inhibition by a compound was calculated using a JCV infection rate instead of using total number of JCV infected cells (e.g., VP1+ cells). Percent JCV Inhibition=100%*(1−(% JCV+ cells with a compound−% JCV+ cells in positive control)/(% JCV+ cells in positive control−% JCV+ cells in negative control). The positive control is the cells infected with the virus in the absence of any compound, negative control are the cells not infected with any virus. The number of JCV+ cells in the negative control samples quantitated by Cellomics ArrayScan were always <1% of the number of JCV+ in the positive control. The percent of JCV DNA inhibition was calculated as 100%*(1−(JCV copy# with a compound−JCV copy# in positive control)/JCV copy# in positive control. Zero copies of JCV genome were detected in no-infected negative control samples. For high throughput screening of compounds, the Z-factor=1−3*(($\sigma$p+$\sigma$n)/|$\mu$p−$\mu$n|; the mean ($\mu$) and standard deviation ($\sigma$) of both the positive (p) and negative (n) controls (Zhang, Chung et al. 1999) were calculated. Intraplate intragroup CV was always below 20% and Z'>0.5. $IC_{50}$ values were calculated using Prism software (GraphPad Software Inc., USA).

Primary Screen: JC Viral Infection Assay

In order to identify the drugs with anti-JCV activity, a commercially available collection of approximately 2000 approved drugs and bioactive compounds called the SPECTRUM collection were screened for anti-JCV activity in an in vitro viral infectivity assay (Pho, Ashok et al. 2000). As a primary screen, the inhibition of the viral infection rate was monitored in a human fetal astroglial cell line (SVG-A) infected with the JCV strain Mad1/SVE$\Delta$. The SVG-A cell line (Major, Miller et al. 1985) was chosen for the primary screening assay, as it is one of the few available cell lines permissive for JC viral replication. Mad1/SVE$\Delta$JCV strain is a wild type Mad-1 virus originally isolated from the PML patient that had its regulatory non-coding region replaced with SV40 regulatory region (Vacante, Traub et al. 1989). That insertion had been demonstrated to extend species and cell-type host range of the virus. Infection of SVG-A cells with Mad1/SVE$\Delta$JCV strain allows for very fast viral replication and detection of virally infected cells within 3 days of infection unlike 6-15 days need with other cell types and viral strains.

Figure 3:
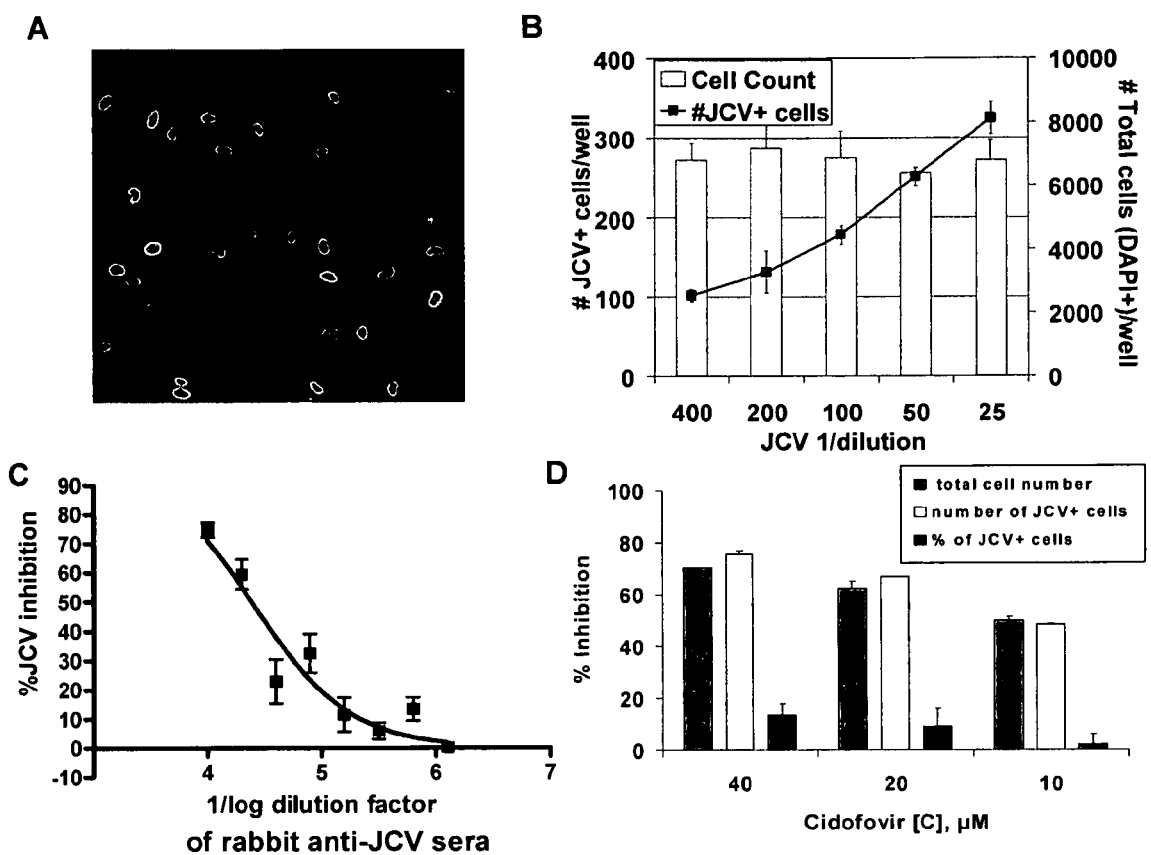
FIG. 3 illustrates a non-limiting embodiment of detection and measurement of cellular infection with JCV, panel (A) shows cells infected with JCV, panel (B) shows the number of infected cells plotted against the dilution factor of the viral stock used to infect the cells, panels (C) and (D) illustrate the inhibition of JCV in the presence of various dilutions of JCV neutralizing antiserum or cidofovir.

Uniformity of a cell line, consistent infection rate and relatively short assay time are all important factors in creating a robust assay for screening of a large number of compounds. To facilitate screening of the large compound collection, this JCV infectivity assay (Pho, Ashok et al. 2000) was used in a 96-well format and a Cellomics ArrayScan was used to measure JCV replication. FIG. 3 shows the detection and measurement of cellular infection with JCV. In FIG. 3A SVG-A cells infected with JCV strain Mad1/SVE$\Delta$ 3 days earlier were fixed and stained with murine monoclonal antibodies specific for VP1 protein (green staining). The total cells present in the culture were visualized with DAPI DNA nuclear staining (blue) and picture was taken with Cellomics ARRAYSCAN® camera at ×20 magnification. FIG. 3B illustrates the number of infected cells (e.g., VP1+ cells) per group plotted against the dilution factor of the viral stock used to infect the cells (mean±SD, n=2). The total number of cells (bars) is similar for all groups. FIGS. 3C and 3D illustrate results for cells that were infected in the presence of various dilutions of JCV neutralizing antiserum or cidofovir. Three days later cells were fixed; stained and total number of VP1+ cells and DAPI+ events per treatment group was enumerated using Cellomics ARRAYSCAN®.

In this system infected cells can be identified by immunofluorescent staining with antibodies specific for JCV capsid protein VP1. Total number of cells in culture was visualized via staining with DNA stain DAPI (FIG. 3A). ARRAYSCAN® was used to identify and count every single event in the assay well, routinely counting 300-800 VP1+ cells and 8,000-16,000 DAPI+ events per well in a 96-well plate, thus minimizing variability due to non-uniform cell growth pattern and/or intrawell viral spread and producing a very consistent result. As can be seen from FIG. 3B, the number of infected cells (e.g., VP1+ cells) at the end of culture period is proportional to the number of infectious viral particles used to infect the cell culture. In these experiments, the highest dilution of the viral stock that was convenient for application was used. Using neutralizing rabbit anti-JCV serum as a positive control for viral inhibition it also was shows that the assay responds to viral inhibition in a predictive fashion (FIG. 3C).

During screening of the library for antiviral activity at single dose (10 $\mu$M), it was discovered that some of the compounds that most dramatically inhibited the number of virally infected cells (e.g., VP1+ cells) also dramatically reduced the total number of cells (e.g., DAPI+ events) likely due to their cytotoxic/cytostatic effects. To determine whether a particular compound had decreased the number of virally infected cells not just due its cytotoxic effect but due to its antiviral effect, the percent of viral inhibition by a compound was calculated using the JCV infection rate (e.g., % JCV+ cells=((total # VP1+ cells)/(total # DAPI+ cells))*100%) rather than total number of JCV infected cells (e.g., the total number of VP1+ cells). In this system JCV infection leads to 4-7% of all cells being infected in 72 hours. As can be seen from the example of treatment with cidofovir, a drug tested for efficacy against PML (FIG. 3D), while it inhibited the number of infected cells in culture they also inhibited the total number of cells in culture to the same degree so the percent inhibition of infection rate (e.g., % JCV+ cells) was not significant. Similar effect was observed with other drugs with well reported cytotoxic effects, e.g., Mytomicin C and cytarabine (data not shown).

Drug Screening and Selection

Figure 4:
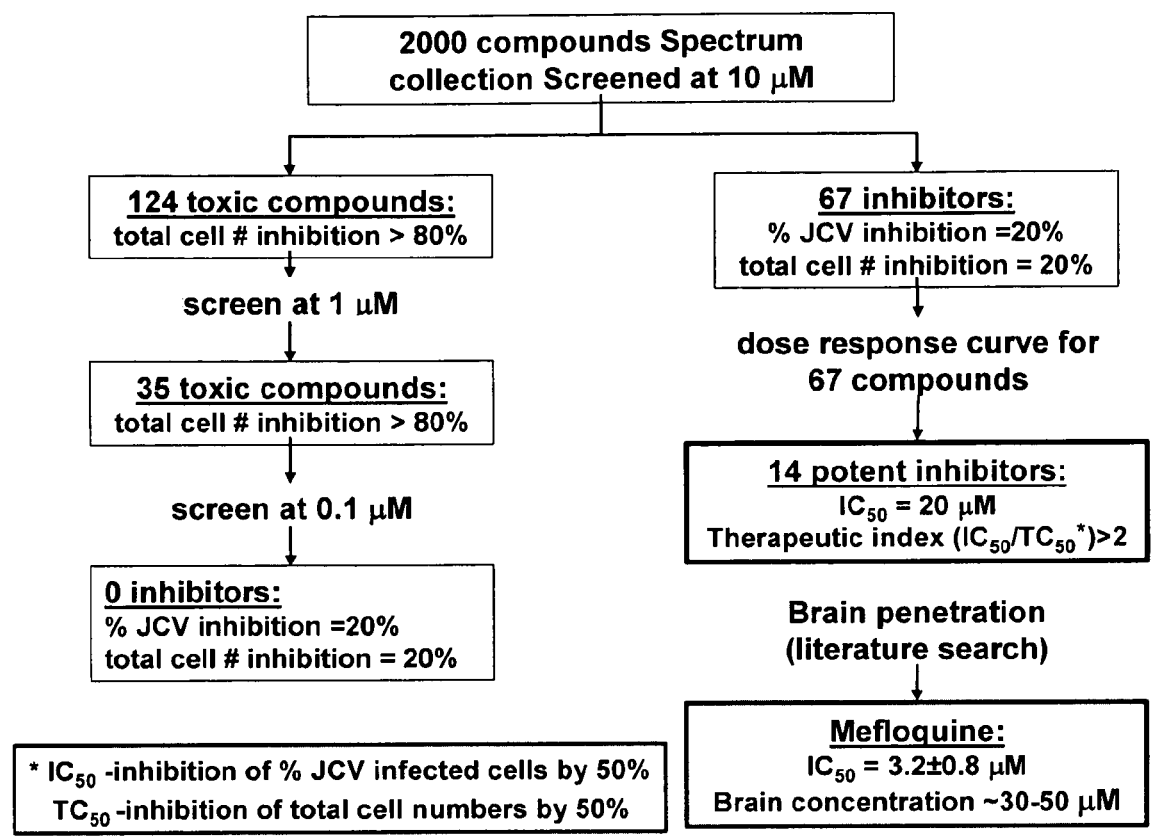
FIG. 4 illustrates a non-limiting embodiment of a flow chart for compound screening.

Following screening the library at a single compound concentration of 10 $\mu$M, a number of drugs and compounds that effectively inhibited JCV infection rate by >20% without significant cell toxicity (<20% total cell number inhibition) were identified (FIG. 4). A level of 20% was chosen as a cut off for the first pass screening because the CV of the assay was consistently <20%. 67 compounds matched those criteria (Table 1) and were subsequently tested in the same assay across a full dose response curve to further evaluate their therapeutic potential. Based on the results from full dose curves 14 drugs proved to be effective, demonstrating >90% inhibition of the virally infected cells ($IC_{50}$<20 $\mu$M) without statistically significant cell toxicity (<20% total cell number inhibition) at those concentrations (Table 3). Only the drugs that did not reduce total cell numbers were selected in order to diminish the chance of confounding an anti-viral effect of the drug with its cytotoxic/cytostatic effect. The compounds that had reduced total cell number by >80% were retested at the lower concentrations, but none were identified that demonstrated clear anti-JCV effect without concomitant cytotoxic/cytostatic effect (FIG. 4). FIG. 4 shows the flow chart for SPECTRUM collection screening. The primary assay employed an SVG-A cell line and JCV Mad1/SVE$\Delta$ viral strain. The assay was performed as described for FIG. 3 (*$IC_{50}$-inhibition of % JCV infected cells by 50%; $TC_{50}$-inhibition of total cell numbers by 50%).

The published literature was reviewed for information on pharmacokinetics and brain distribution of these drugs in humans and in animal models. Since JC virus uncontrollably replicates in the oligodendrocytes and astrocytes of the effected individuals during PML but not all drugs are capable of crossing blood brain barrier it would be advantageous for any potential PML therapy if the drug candidate is capable of achieving efficacious concentration in the brain. Based on the published literature (Table 3), mefloquine had been demonstrated to accumulate in the brains of treated patients at the level of its in vitro efficacious concentration (FIG. 3A; $IC_{50}=3.9\pm2.1$ μM). Brain concentration of mefloquine based on postmortem brain analysis of people taking the drug prior to their deaths was 35-50 nmol per gram of brain tissue, which could be approximated as 35-50 μM (Jones, Kunsman et al. 1994; Pham, Nosten et al. 1999). This indicates that potentially efficacious doses of mefloquine can be achieved in the brain patients who would be receiving approved doses of the drug.

Characterization of Mefloquine Activity in Primary Cell Culture

Figure 5:
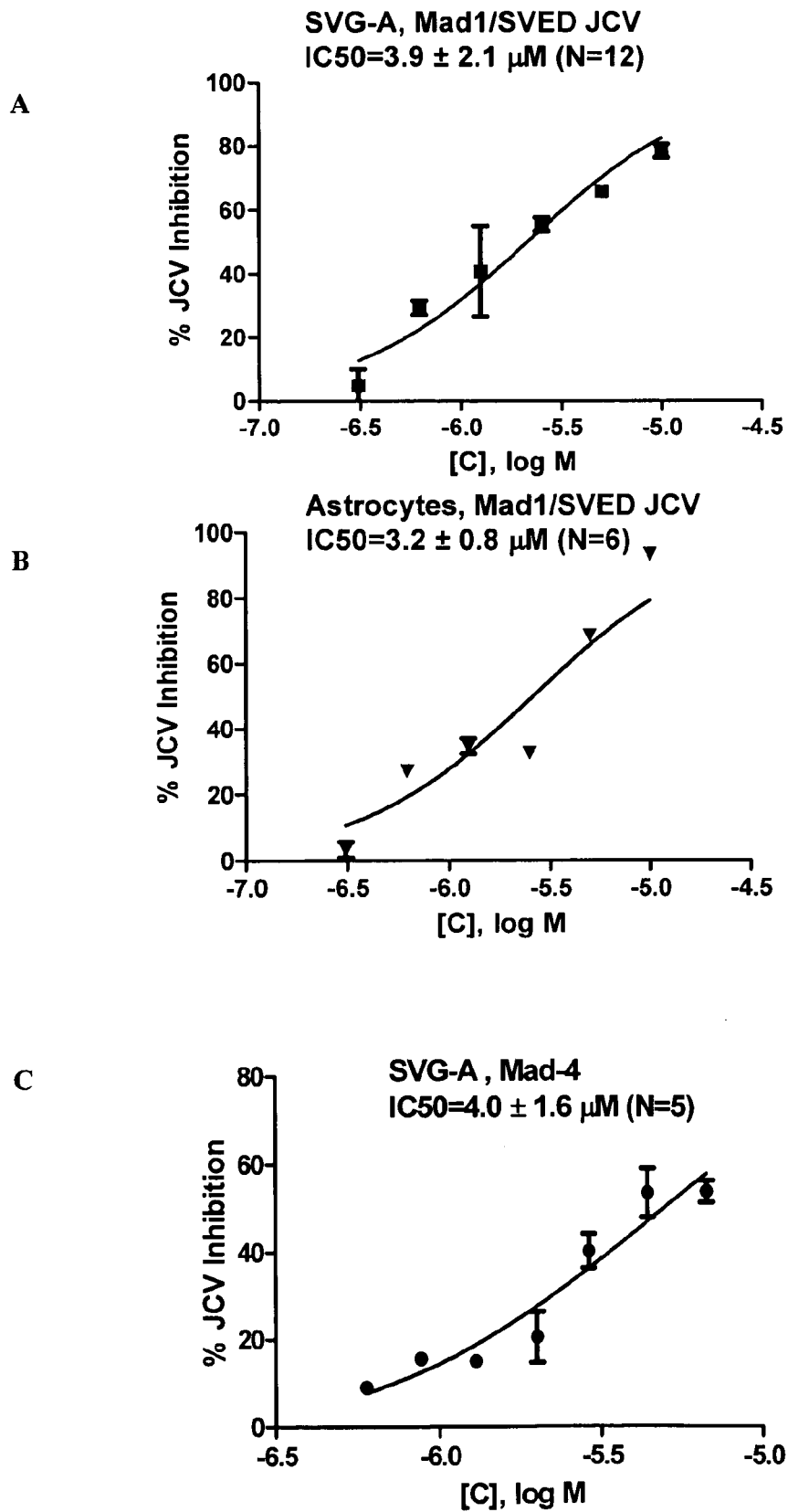
FIG. 5 illustrates a non-limiting embodiment of the efficacy of mefloquine against two different viral strains, panel (A) illustrates SVG-A cells infected with Mad1/SVEΔ JCV virus, panel (B) illustrates primary human fetal astrocytes infected with Mad1/SVEΔ JCV, and panel (C) illustrates SVG-A cells infected with JCV strain Mad-4.

In order to further characterize the effect of mefloquine in JC virus infectivity, experiments were performed to evaluate whether the JCV inhibitory effect of mefloquine was dependent on the cell line used in the primary screen. Since SVG-A cells is a cell line propagated in vitro for many generations, and is transformed with SV40 large T antigen that can enhance JCV replication, experiments were performed to evaluate whether mefloquine is capable of inhibiting viral replication in cells that more closely resemble JCV target in human brain and do not express SV40 TAg. Since in vitro infection culture of primary oligodendrocytes, a primary JCV target during PML, is not established, the JCV infection of human fetal astrocytes was used to test the ability of mefloquine to inhibit the viral infection in primary cell culture. FIG. 5 shows the efficacy of mefloquine against two different viral strains (Mad1 and Mad4) in two different cell types (SVG-A and primary astrocytes). FIG. 5A illustrates SVG-A cells with Mad1/SVEΔ JCV (n=12) virus. FIG. 5B illustrates primary human fetal astrocytes with Mad1/SVEΔ JCV. FIG. 5C illustrates SVG-A cells with JCV strain Mad-4 (n=5). % JCV Inhibition was calculated as 100%*(1–(% JCV+ cells with a compound–% JCV+ cells in negative control)/(% JCV+ cells in positive control–% JCV+ cells in negative control). Inhibition of total cell numbers (e.g., DAPI+ events) was less than 20% for all drug concentrations plotted. Unless otherwise noted, one representative graph out of the number presented on the graph is shown. $IC_{50}$ are calculated as an average of all those experiments. As can be seen from FIG. 5A, mefloquine inhibits JCV infection of primary human fetal astrocytes with essentially the same efficacy as it inhibits viral infection in SVG-A cells. This result shows that anti-JCV effect of mefloquine is not dependent on cell type being infected by the virus, and that mefloquine is effective at inhibiting the virus in its "natural" setting of glial cell infection.

Characterization of Mefloquine Activity on Different JC Viral Strains

Experiments were also performed to determine whether the inhibitory effect of mefloquine is observed with other JC viral strains, and is not limited to Mad1/SVEΔ JCV strain used in the primary screening assay. The primary screen was conducted with the Mad1/SVEΔ JCV strain because of its fast replication in tissue culture. However, this viral strain contains a transcription regulatory region (non-coding) from its polyomavirus family member SV40. To ensure that mefloquine's anti-viral activity is not limited only to the virus with this modification, mefloquine's ability to inhibit an unmodified JCV strain, wild type virus Mad4 that was originally isolated from a PML patient (Major, Vacante et al. 1987; Frye, Trebst et al. 1997), was tested. As can be seen from FIG. 5C, based on the results from 5 independent experiments, mefloquine inhibits Mad4 infection of SVG-A cells with the same efficacy as Mad1/SVEΔ infection. This result demonstrates that anti-JCV effect of mefloquine does not depend on the viral strain.

Effect on JCV Viral DNA Replication

Figure 6:
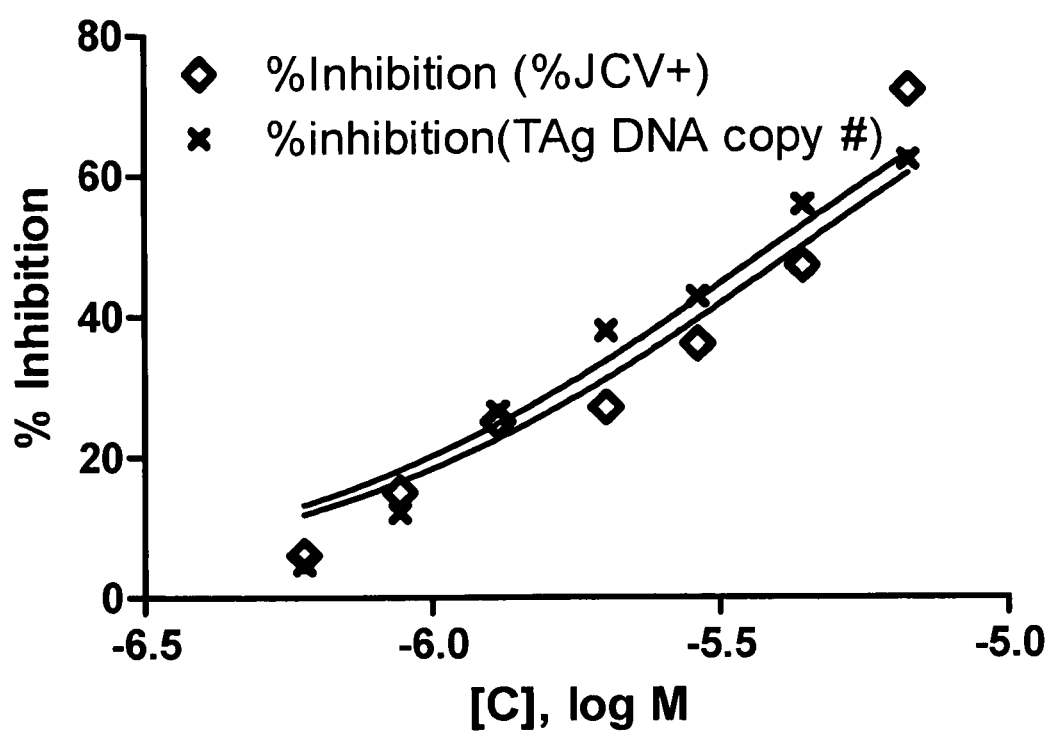
FIG. 6 illustrates a non-limiting embodiment of the effect of mefloquine on JCV DNA replication.

In order to better understand the mechanism of action of mefloquine and address whether this drug inhibits rate of cell infection by JC virus via inhibition of viral DNA replication, viral DNA was quantified using qPCR and a probe set specific for JCV T Antigen. As can be seen from FIG. 6, the percent of JCV DNA inhibition by mefloquine almost overlaps the percent of infection rate inhibition. A linear correlation between the viral DNA copy number and a number of virally infected cells was observed (data not shown). This result demonstrates that mefloquine inhibits infection rate via its inhibition of viral DNA replication, and not VP1 protein expression. FIG. 6 shows the effect of mefloquine on JCV DNA replication. SVG-A cells were infected with Mad1/SVEΔ JCV 3 days earlier in the presence of various drug concentrations. % JCV DNA inhibition (◇) was calculated using JCV copy numbers determined by qPCR with a probe set specific for TAg. Inhibition of infection rate (x) was measured in a replicate plate as described herein.

Effect of Mefloquine on Established JCV Infection

Figure 7:
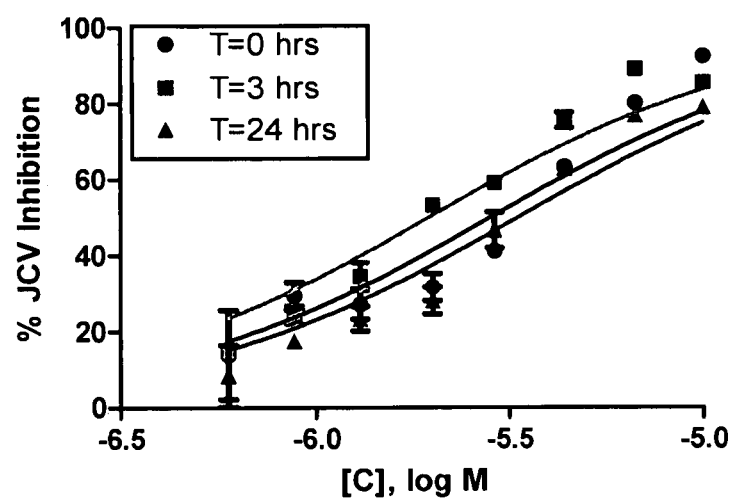
FIG. 7 illustrates a non-limiting embodiment of the efficacy of mefloquine against JCV infection.

Experiments were performed to demonstrate that mefloquine is effective against established JCV infection. While it is apparent from the above experiments that mefloquine is effective at inhibiting JCV infection when added at the same time as the virus, it was not clear from those experiments whether mefloquine inhibited viral entry into the cells, or the viral life cycle in the cell. Since during PML many cells are already infected with JC virus, in some embodiments a drug candidate for treatment of PML may be selected as one that can inhibit viral life cycle in already infected cells. As seen from FIG. 7, when added in 3 or 24 hours post infection, mefloquine was just as effective at inhibiting cell infection as it was when added to the cells together with the virus. Since most of the virus enters the cells within 1 hour, and all of the virus enters the cells within first 24 hours after infection (unpublished data), this result shows that mefloquine is effective in inhibiting viral replication in already infected cells. In FIG. 7 various concentration of the drug were added to the culture of primary human fetal astrocytes infected with JC virus at the same time as virus (circles; T=0), 3 hours after virus addition (squires; T=3 h), or 24 hours after (triangles; T=24 h). Ten days after infection with the virus cells were fixed and number of virally infected cells was enumerated. Results of a representative experiment out of 4 different experiments with primary astrocytes or SVG-A cells are shown.

Characterization of Mefloquine Enantiomers

Figure 8:
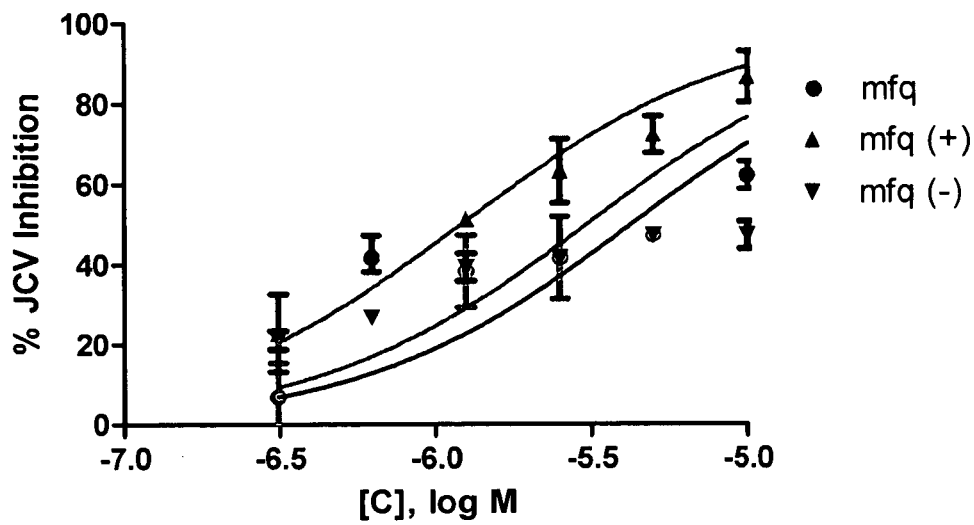
FIG. 8 illustrates non-limiting embodiments of the efficacy of different isomers of mefloquine.
Figure 8:
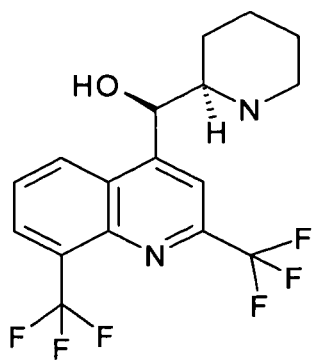
Figure 8:
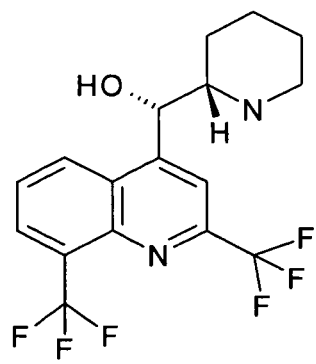
Figure 9:
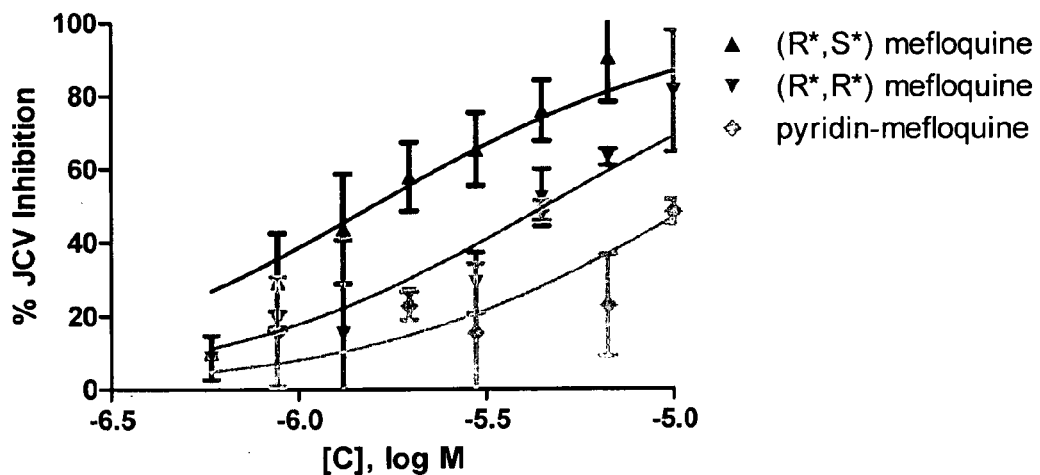
FIG. 9 illustrates non-limiting embodiments of the efficacy of different isomers of mefloquine.
Figure 9:
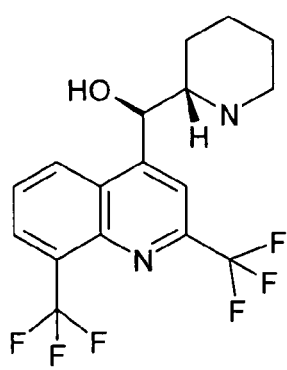
Figure 9:
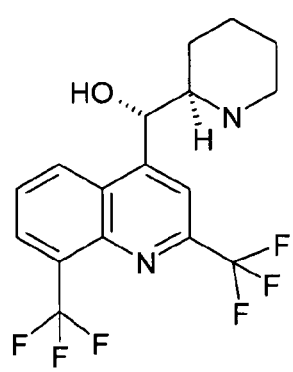
Figure 9:
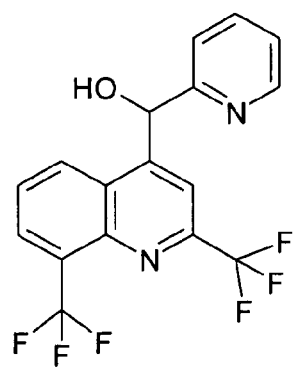
Figure 10:
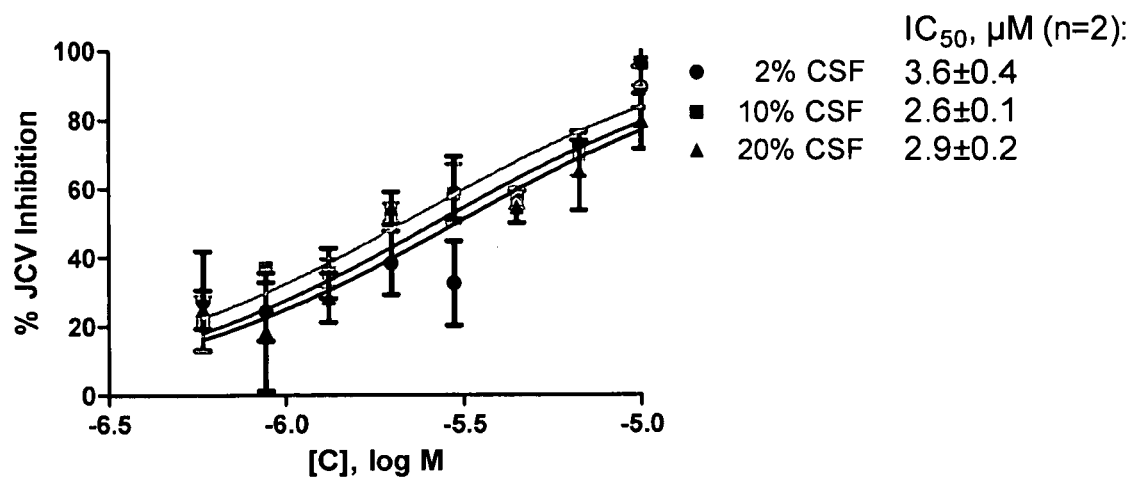
FIG. 10 shows that mefloquine anti-JCV activity is not inhibited by cerebrospinal fluid (CSF)

Mefloquine is a racemic mix of (+) and (−) enantiomers of (R*,S*)-α-2-piperidinyl-2,8-bis (trifluoromethyl)-4-quinolinemethanol hydrochloride (FIG. 8). FIG. 8 shows the efficacy of different isomers of mefloquine. FIG. 8A shows $IC_{50}$s and structure of (R,S) and (S,R) enantiomers constituting drug racemate commercial mefloquine. (+) and (−) enantiomers were separated from a racemate via chiral chromatography and added to SVG-A cells simultaneously with JCV strain Mad1/SVEΔ 3 days earlier. After fixation and staining total number of VP1+ cells and DAPI+events per treatment group was enumerated using Cellomics ARRAYSCAN®. A representative experiment out of six performed is shown. While there is a minimal difference between the activities of the enantiomers against malaria (Basco, Gillotin et al. 1992; Brocks and Mehvar 2003), the (−) enantiomer is much more potent in antagonistic activity against A2a receptor (Weiss, Benwell et al. 2003). The two enantiomers also display different pharmacokinetics and brain penetration properties (Bourahla, Martin et al. 1996; Baudry, Pham et al. 1997). In order to better understand the anti-JCV effects of these two components of the marketed mefloquine racemate, each enantiomer from a racemate was separated using chiral chromatography and compared them in a JCV inhibition assay. As can be seen from FIG. 8, both enantiomers have very similar efficacy in inhibiting JC virus. FIG. 9 shows the efficacy of different isomers of mefloquine and 2,8-Bis-trifluoromethyl-quinolin. The compounds were added to SVG-A cells simultaneously with JCV strain Mad1/SVEΔ 3 days earlier. After fixation and staining total number of VP1+ cells and DAPI+ events per treatment group was enumerated using Cellomics ARRAYSCAN ®. A representative experiment out of six performed is shown. The illustrated compounds all inhibited JC virus replication. S,S-mefloquine and R,R-mefloquine have similar $IC_{50}$ similar to R,S-mefloquine and S,R-mefloquine, while a structurally related compound that has a aromatized ring has a slightly higher $IC_{50}$. FIG. 10. shows that mefloquine anti-JCV activity is not inhibited by cerebrospinal fluid (CSF).

Based on this result and on the reported brain concentration for mefloquine enantiomers (Baudry, Pham et al. 1997) it can be concluded that mefloquine can be administered at concentrations efficacious in JCV inhibition in the brain of patients.

Furthermore, lack of significant differences between anti-JCV activities of the enantiomers implies that this effect is not mediated by A2a receptor.

Mefloquine has been identified as a potential treatment for PML based on the results of screening a commercially available collection of approved drugs and bioactive compounds in in vitro JC viral infection assay. Follow-up experiments demonstrated that the effect of mefloquine is not limited to one cell type or a single viral strain. Furthermore, mefloquine is capable of inhibiting viral replication in cells already infected with the virus. Both (+) and (−) enantiomers of mefloquine racemate were almost equipotent at inhibiting JCV infection, indicating that isolating individual enantiomers would not improved the benefit of the existing drug. In addition, the literature shows that mefloquine crosses the blood brain barrier and can accumulate in the brain at the in vitro defined efficacious concentration for inhibition of JC viral infectivity. Although no animal model is available for PML, the in vitro results and literature data show that mefloquine is an effective anti-JCV therapy.

TABLE 3

Selected inhibitors (anti-JCV IC50 ≤20 μM, Therapeutic index (IC50/TC50) <0.5)

| MOLENAME | THERAPY | STATUS | $TC_{50}$, μM | $IC_{50}$, μM | Brain, μM | plasma Cmax, μM | References for PK data |
|---|---|---|---|---|---|---|---|
| ISOTRETINON | antiacne, antineoplastic | USP, INN, BAN | ND | 4.4 | | 1100 ng/ml | (Clamon, Chabot et al. 1985; Colburn and Gibson 1985) |
| MEFLOQUINE | antimalarial | USAN, INN, BAN | 16.1 | 4.0 | 30-50 | 6.0 | (Jones, Kunsman et al. 1994; Pham, Nosten et al. 1999) |
| DICLOFENAC SODIUM | antiinflammatory | USP, JAN | 30.5 | 8.3 | | | |
| DILTIAZEM HYDROCHLORIDE | Ca channel blocker | USP, INN, BAN, JAN | >40 | 8.5 | | | |
| FUSIDIC ACID | antibacterial | USAN, INN, BAN | ND | 8.6 | 1 μg/ml | 10-90 μg/ml | (Mindermann, Zimmerli et al. 1993; Turnidge 1999) |
| MICONAZOLE NITRATE | antifungal (topical) | USP, JAN | 22.9 | 8.6 | nd | 10 ng/ml | (Stevens, Konsil et al. 2002) |
| MEFENAMIC ACID | antiinflammatory, analgesic | USP, INN, BAN, JAN | ND | 10.9 | 0.8 μg/ml # | 10-20 μg/ml | (Glazko 1966; Fukuda, Kitaichi et al. 2005) |
| FLUNIXIN MEGLUMINE | analgesic, antiinflammatory | USP, veterinarian | 47.7 | 16.6 | | | |
| PROPANIL | | herbicide | >40 | 7.8 | | | |
| DEHYDROABIETAMIDE | NA | NA | >40 | 13.0 | | | |
| DIFFRACTIC ACID | NA | NA | >40 | 14.4 | | | |
| HARMANE | NA | NA | >40 | 14.4 | | | |
| XANTHONE | NA | NA | ND | 16.8 | | | |
| METHOXYVONE | NA | NA | >40 | 17.2 | | | | animal data
USP, United States Pharmacopeia
INN, International Nonproprietary Name
BAN, British Approved Name
JAN, Japanese Approved Name Clamon, G., G. G. Chabot, et al. (1985). "Phase I study and pharmacokinetics of weekly high-dose 13-cis-retinoic acid." *Cancer Res* 45(4): 1874-8.
Colburn, W. A. and D. M. Gibson (1985). "Isotretinoin kinetics after 80 to 320 mg oral doses." *Clin Pharmacol Ther* 37(4): 411-4.
Fukuda, M., K. Kitaichi, et al. (2005). "Altered brain penetration of diclofenac and mefenamic acid, but not acetaminophen, in Shiga-like toxin II-treated mice." *J Pharmacol Sci* 97(4): 525-32.
Glazko, A. J. (1966). "Experimental observations on flufenamic, mefenamic and meclofenamic acids. 3 Metabolic disposition." *Ann Phys Med* Suppl: 23-36.
Jones, R., G. Kunsman, et al. (1994). "Mefloquine distribution in postmortem cases." *Forensic Sci Int* 68(1): 29-32.
Mindermann, T., W. Zimmerli, et al. (1993). "Penetration of fusidic acid into human brain tissue and cerebrospinal fluid." *Acta Neurochir (Wien)* 121(1-2): 12-4.
Pham, Y. T., F. Nosten, et al. (1999). "Cerebral uptake of mefloquine enantiomers in fatal cerebral malaria." *Int J Clin Pharmacol Ther* 37(1): 58-61.
Stevens, R. E., J. Konsil, et al. (2002). "Bioavailability study of a 1200 mg miconazole nitrate vaginal ovule in healthy female adults." *J Clin Pharmacol* 42(1): 52-60.
Turnidge, J. (1999). "Fusidic acid pharmacology, pharmacokinetics and pharmacodynamics." *Int J Antimicrob Agents* 12 Suppl 2: S23-34.

Example 5

Figure 11:
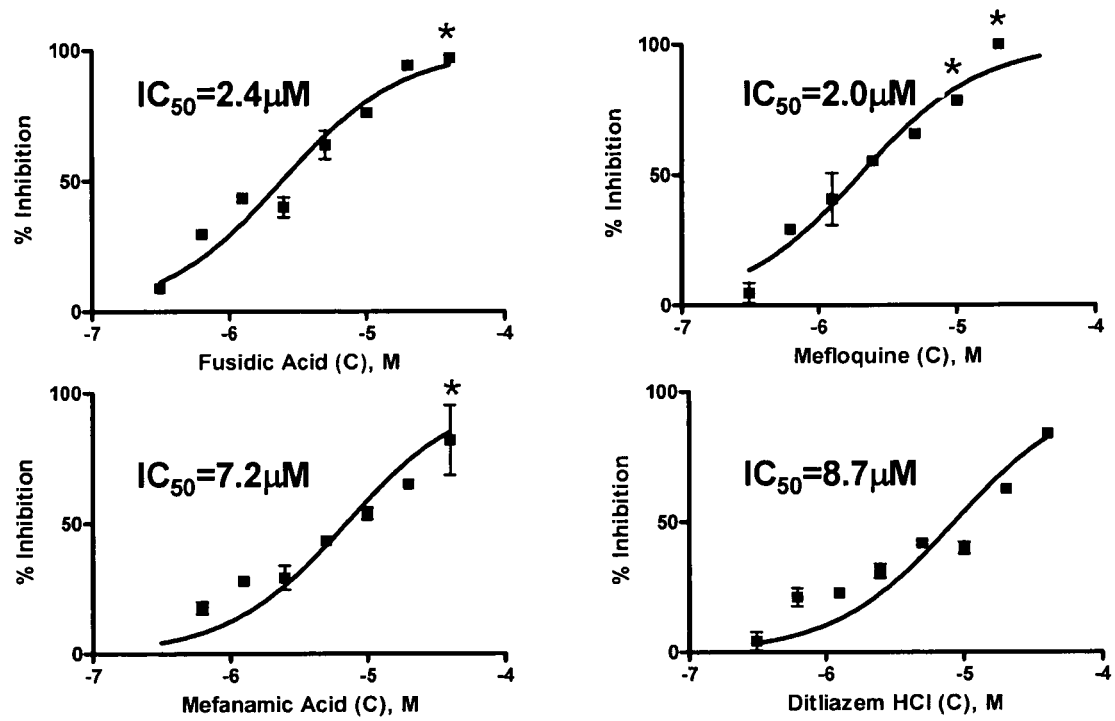
FIG. 11 illustrates non-limiting embodiments of the dose response of drugs with anti-JCV activity.
Figure 12:
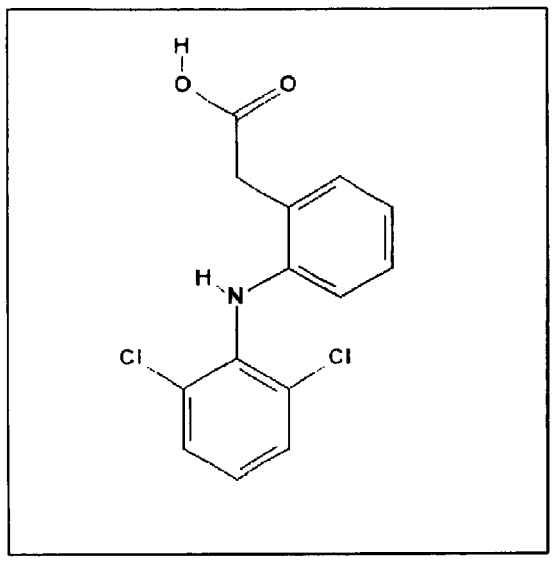
FIG. 12 illustrates non-limiting embodiments of arylalkanoic acid NSAIDs and their anti-JCV activity.
Figure 12:
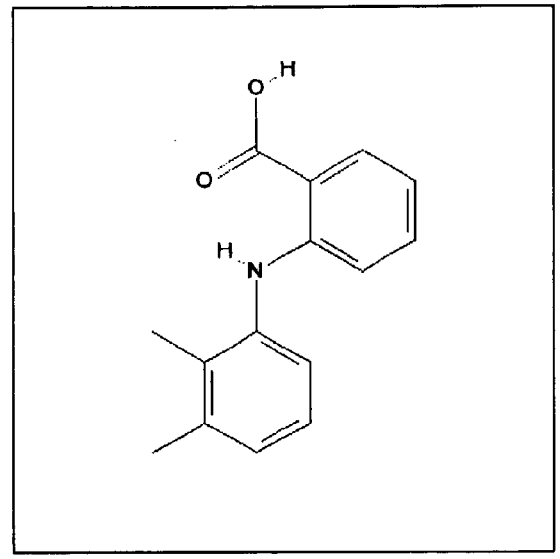
Figure 12:
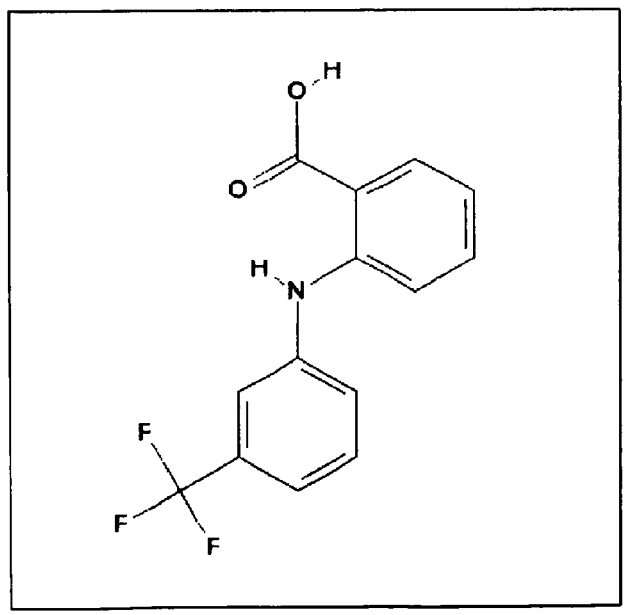
Figure 13:
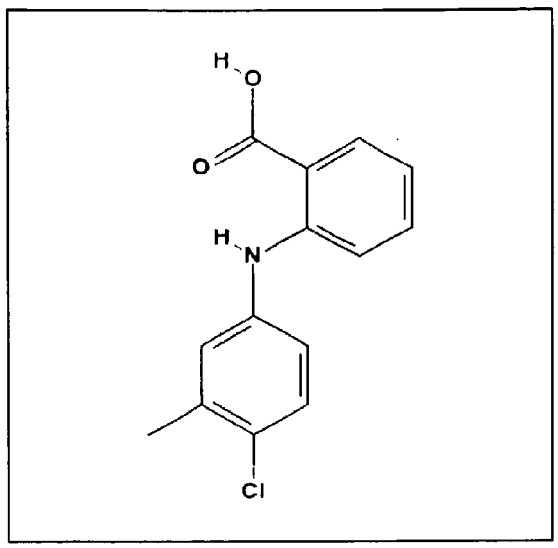
FIG. 13 illustrates non-limiting embodiments of arylalkanoic acid NSAIDs and their anti-JCV activity.
Figure 13:
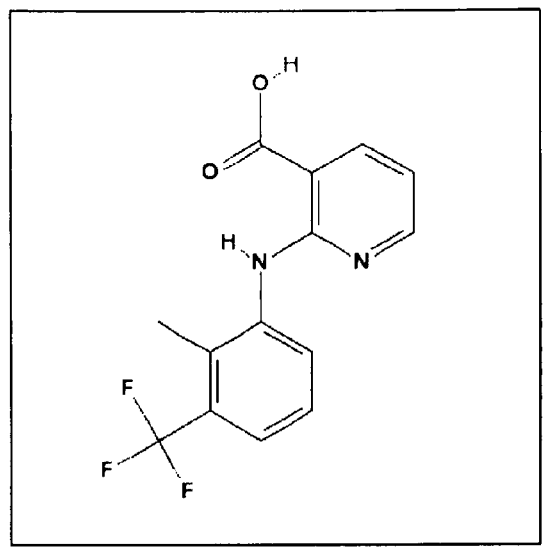
Figure 14:
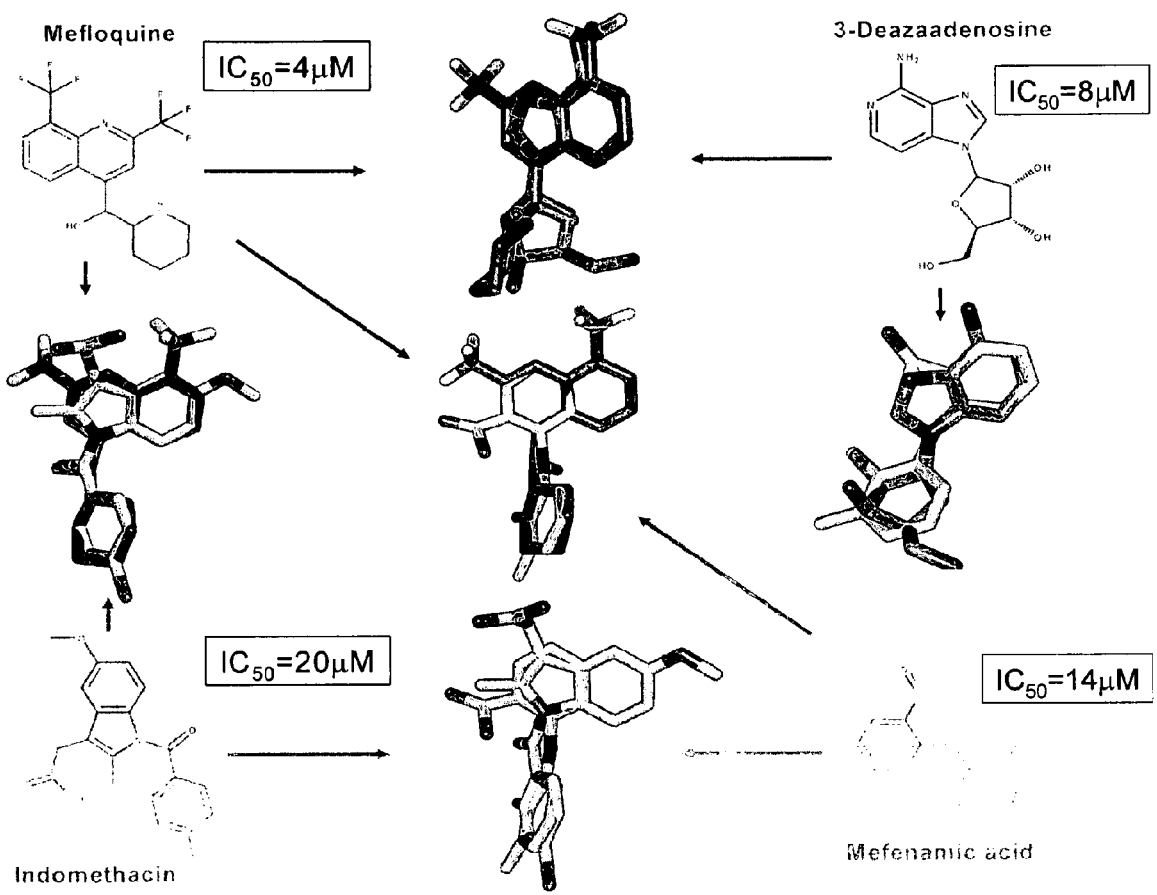
FIG. 14 illustrates non-limiting embodiments of modeling studies with mefloquine and related compounds.

Identification and Characterization of Compounds that are Active Against JC Virus FIG. 11 shows the dose response of several compounds that have anti-JCV activity. FIGS. 12 and 13 show selected arylalkanoic acid NSAIDs and their anti-JCV activity. FIG. 14 shows the result of modeling studies with mefloquine and related compounds and the $IC_{50}$s of a number of compounds structurally related to mefloquine. A pharmacophore-based alignment method Catalyst and shape-based alignment method ROCS were used to study the similarity between the compounds. The overlays below (or above) were derived in ROCS using scoring scheme that combines shape and weighted chemical force-field overlap between molecules. Similar relationships between molecules were detected through pharmacophore matching.

Figure 15:
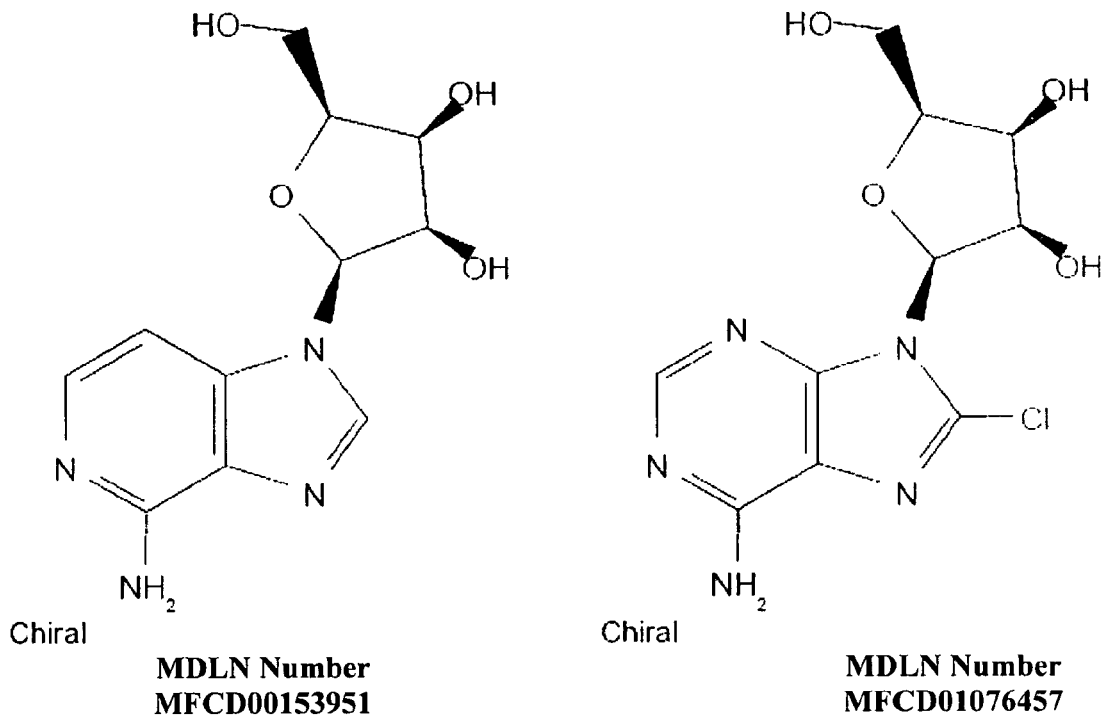
FIG. 15 illustrates non-limiting embodiments of structures of JCV-inhibitor compounds; and, FIG. 16 illustrates non-limiting embodiments of structures of JCV-inhibitor compounds.
Figure 15:
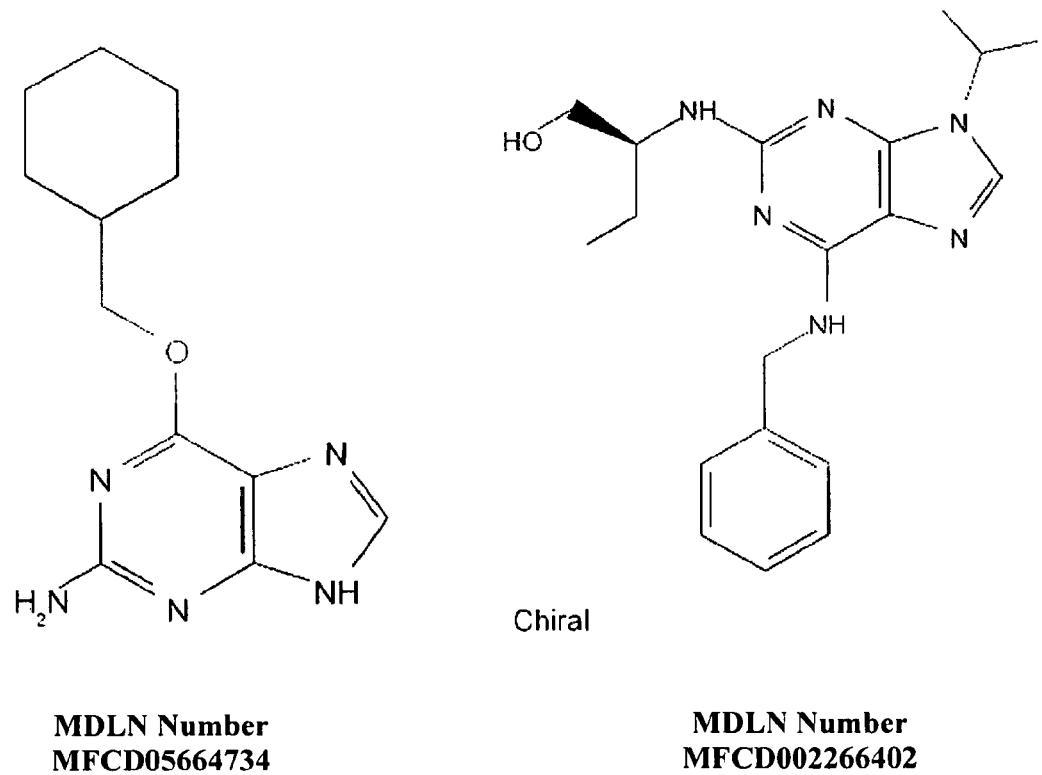
Figure 16:
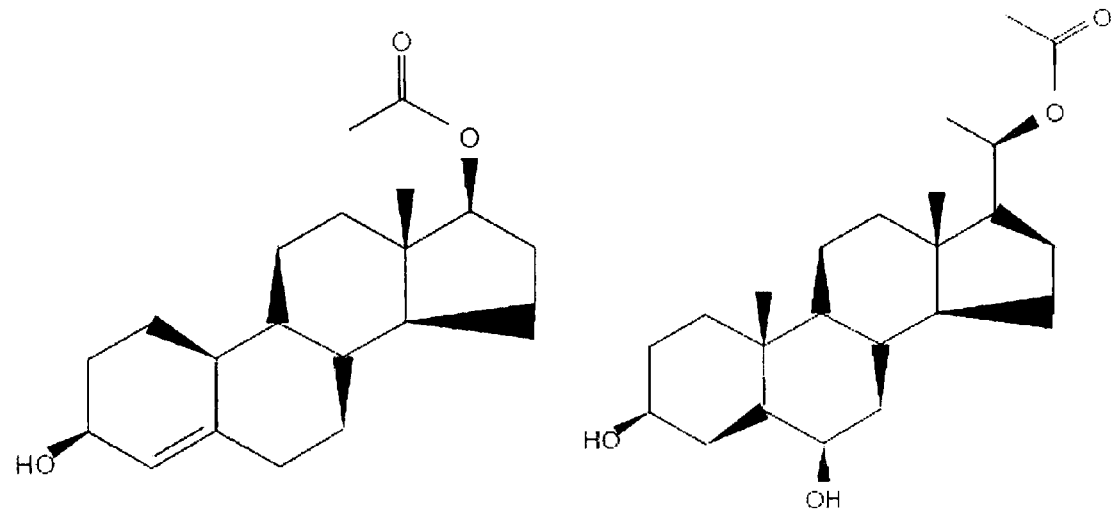
Figure 16:
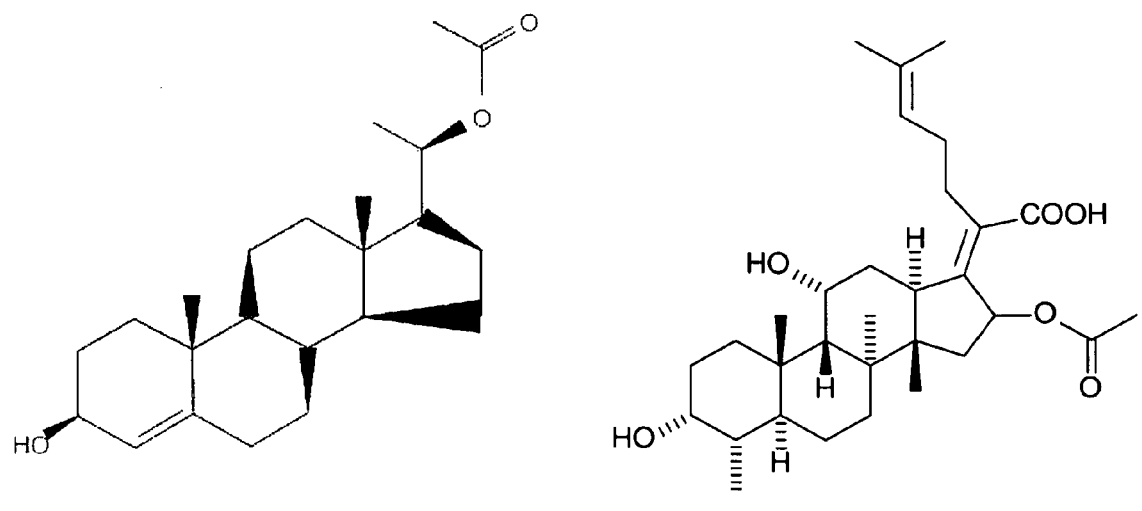

Table 4 shows the anti-JCV activity of a number of structural analogs to mefloquine (See also FIG. 15). Table 5 shows the anti-JCV activity of a number of structural analogs to fusidic acid (See also FIG. 16).

It should be appreciated that any one or more of the structural analogs described herein and/or any one or more of the compounds listed in Tables 1-5 can be used according to methods of the invention if they have suitable properties as described herein.

TABLE 4

Selected compounds from mefloquine functional fingerprint in silico screen

| Structure | MOLREGNO | MDLNUMBER | MOLNAME | CAS# | anti-JCV activity |
|---|---|---|---|---|---|
| Nc1ncnc2n(c(nc12)Cl)C1O C(CO)C(O)C1O | 129461 | MFCD01076457 | 8-CHLOROADENOSINE | 34408-14-5 | Yes |
| Nc1nccc2n(cnc12)C1OC(C O)C(O)C1O | 64582 | MFCD00153951 | 3-DEAZAADENOSINE | 6736-58-9 | Yes |
| Nc1nc2ncnc2c(n1)OCC1C CCCC1 | 289926 | MFCD05664734 | O6-Cyclohexylmethylguanine | | Yes |
| CCC(CO)Nc1nc(c2ncn(c2n 1)C(C)C)NCc1ccccc1 | 182843 | MFCD02266402 | ROSCOVITINE, (S)-ISOMER | | Yes |
| Nc1ncnc2n(cnc12)C1OC(C O)C(O)C1O | 5424 | MFCD00005752 | ADENOSINE | 58-61-7 | No |
| NC1=Nc2n(cnc2C(=O)N1) C1OC(CO)C(O)C1O | 9593 | MFCD00010182 | GUANOSINE | 118-00-3 | No |
| CC(C)C(=O)c1c2n(nc1C(C) C)C=CC=C2 | 123831 | MFCD00864808 | IBUDILAST | 50847-11-5 | No |
| OCC1OC(C(O)C1O)n1cnc 2c(ncnc12)NCc1ccccc1 | 5414 | MFCD00005740 | 6-BENZYLAMINOPURINE RIBOSIDE | 4294-16-0 | NA |
| Nc1c2ncn(c2nc[n+]1[O—]) C1OC(CO)C(O)C1O | 21536 | MFCD00037993 | ADENOSINE-N'-OXIDE | | NA |
| NC1=Nc2n(cnc2C(=O)N1) C1OC(CO)C(O)C1O | 38045 | MFCD00064103 | BETA-L-GUANOSINE | | NA |
| OCC1OC(C(O)C1O)n1cnc 2c(ncnc12)NC1CC2CCC1 C2 | 40907 | MFCD00069271 | (2S)-N6-[2-ENDO-NORBORNYL]ADENOSINE | | NA |
| Cn1cnc2c(ncnc12)NC1CC CC1 | 64492 | MFCD00153844 | N-0840 | | NA |
| Cc1cc(c2nccc(c2c1)C)C | 74766 | MFCD00191505 | 4,6,8-TRIMETHYLQUINOLINE | | NA |
| Nc1nc2ncnc2c(n1)OCc1cc ccc1 | 91708 | MFCD00269931 | O6-BENZYLGUANINE | 19916-73-5 | NA |
| Cc1cc(c2cccc(c2n1)C)C | 93735 | MFCD00272331 | 2,4,8-TRIMETHYLQUINOLINE | 18441-61-7 | NA |
| CN1C(=O)N(C)c2ncn(c2C1 =O)CC1OCCO1 | 123874 | MFCD00865218 | DOXOFYLLINE | 69975-86-6 | NA |
| CC(C)Cn1cnc2c(nc3ccccc3 c12)N | 124036 | MFCD00866946 | IMIQUIMOD | 99011-02-6 | NA |
| CCCCN1C(=O)N(CCCC)c2 ncn(c2C1=O)CC(C)=O | 124063 | MFCD00867152 | DENBUFYLLINE | 57076-71-8 | NA |
| CN1N=C(N)c2cn(c3ncnc1c 23)C1OC(CO)C(O)C1O | 124573 | MFCD00932413 | 6-AMINO-4-METHYL-8-(BETA-D-RIBOFURANOSYL)-4H,8H-PYRROLO[4,3,2-DE]PYRIMIDO[4,5-C]PYRIDAZINE | 35943-35-2 | NA |
| N(c1ccccc1)C1=CC(=Nc2n cnn21)c1ccccc1 | 124680 | MFCD00951199 | BUTTPARK 57\40-37 | | NA |
| CC(C)n1cnc2c(nc(nc12)NC CCO)NCc1ccccc1 | 280770 | MFCD04974145 | 6-BENZYLAMINO-2-(3-HYDROXYPROPYLAMINO)-9-ISOPROPYLPURINE | | NA |
| OC(=O)c1cc2cc(c(cc2c(n1) C(=O)c1ccc(c(c1)O)O)O)O | 280811 | MFCD04974186 | 1-(3',4'-DIHYDROXYBENZOYL)-6,7-DIHYDROXYISOQUINOLINE-3-CARBOXYLIC ACID | | NA |

TABLE 5

Selected fusidic acid analogs

| Structure | MOLREGNO | MDLNUMBER | MOLNAME | anti-JCV activity |
|---|---|---|---|---|
| CC(=O)OC1CCC2C3CCC4= CC(O)CCC4C3CCC12C | 93067 | MFCD00271609 | 4-ESTREN-3-BETA, 17-BETA-DIOL 17-ACETATE | Yes |
| CC(OC(C)=O)C1CCC2C3CC(O) C4CC(O)CCC4(C)C3CCC12C | 93343 | MFCD00271896 | 5-BETA-PREGNAN-3-ALPHA, 6-ALPHA, 20-BETA-TRIOL 20-ACETATE | Yes |
| CC(OC(C)=O)C1CCC2C3CC C4=CC(O)CCC4(C)C3CCC12 C | 93383 | MFCD00271937 | 4-PREGNEN-3-BETA, 20-BETA-DIOL 20-ACETATE | Yes |
| CC(OC(C)=O)C1CCC2C3CC(O) C4CC(O)CCC4(C)C3CCC1 2C | 93342 | MFCD00271895 | 5-BETA-PREGNAN-3-ALPHA, 6-ALPHA, 20-ALPHA-TRIOL 20-ACETATE | No |
| CC(CC(O)=O)C1CCC2C3C(C C4CC(O)CCC4(C)C3CC(OC(C) =O)C12C)OC(C)=O | 234323 | MFCD03695615 | 23-NOR-5-BETA-CHOLANIC ACID-3-ALPHA, 7-ALPHA, 12-ALPHA-TRIOL 7,12-DIACETATE | No |

REFERENCES

Aksamit, A. J. (2001). "Treatment of non-AIDS progressive multifocal leukoencephalopathy with cytosine arabinoside." J Neurovirol 7(4): 386-90.

Atwood, W. J. (2001). "A combination of low-dose chlorpromazine and neutralizing antibodies inhibits the spread of JC virus (JCV) in a tissue culture model: implications for prophylactic and therapeutic treatment of progressive multifocal leukencephalopathy." J Neurovirol 7(4): 307-10.

Atwood, W. J., L. Wang, et al. (1995). "Evaluation of the role of cytokine activation in the multiplication of JC virus (JCV) in human fetal glial cells." J Neurovirol 1(1): 40-9.

Basco, L. K., C. Gillotin, et al. (1992). "In vitro activity of the enantiomers of mefloquine, halofantrine and enpiroline against *Plasmodium falciparum*." Br J Clin Pharmacol 33(5): 517-20.

Baudry, S., Y. T. Pham, et al. (1997). "Stereoselective passage of mefloquine through the blood-brain barrier in the rat." J Pharm Pharmacol 49(11): 1086-90.

Bourahla, A., C. Martin, et al. (1996). "Stereoselective pharmacokinetics of mefloquine in young children." Eur J Clin Pharmacol 50(3): 241-4.

Brocks, D. R. and R. Mehvar (2003). "Stereoselectivity in the pharmacodynamics and pharmacokinetics of the chiral antimalarial drugs." Clin Pharmacokinet 42(15): 1359-82.

Cinque, P., S. Bossolasco, et al. (2003). "The effect of highly active antiretroviral therapy-induced immune reconstitution on development and outcome of progressive multifocal leukoencephalopathy: study of 43 cases with review of the literature." J Neurovirol 9 Suppl 1: 73-80.

Cinque, P., I. J. Koralnik, et al. (2003). "The evolving face of human immunodeficiency virus-related progressive multifocal leukoencephalopathy: defining a consensus terminology." J Neurovirol 9 Suppl 1: 88-92.

Clifford, D. B., C. Yiannoutsos, et al. (1999). "HAART improves prognosis in HIV-associated progressive multifocal leukoencephalopathy." Neurology 52(3): 623-5.

Crowder, C. D., K. A. Gyure, et al. (2005). "Successful outcome of progressive multifocal leukoencephalopathy in a renal transplant patient." Am J Transplant 5(5): 1151-8.

Frye, S., C. Trebst, et al. (1997). "Efficient production of JC virus in SVG cells and the use of purified viral antigens for analysis of specific humoral and cellular immune response." J Virol Methods 63(1-2): 81-92.

Gasnault, J., P. Kousignian, et al. (2001). "Cidofovir in AIDS-associated progressive multifocal leukoencephalopathy: a monocenter observational study with clinical and JC virus load monitoring." J Neurovirol 7(4): 375-81.

Hall, C. D., U. Dafni, et al. (1998). "Failure of cytarabine in progressive multifocal leukoencephalopathy associated with human immunodeficiency virus infection. AIDS Clinical Trials Group 243 Team." N Engl J Med 338(19): 1345-51.

Jones, R., G. Kunsman, et al. (1994). "Mefloquine distribution in postmortem cases."

Forensic Sci Int 68(1): 29-32.

Knowles, W. A. (2006). "Discovery and epidemiology of the human polyomaviruses BK virus (BKV) and JC virus (JCV)." Adv Exp Med Biol 577: 19-45.

Liu, C. K., A. P. Hope, et al. (1998). "The human polyomavirus, JCV, does not share receptor specificity with SV40 on human glial cells." J Neurovirol 4(1): 49-58.

Major, E. O., A. E. Miller, et al. (1985). "Establishment of a line of human fetal glial cells that supports JC virus multiplication." Proc Natl Acad Sci USA 82(4): 1257-61.

Major, E. O., D. A. Vacante, et al. (1987). "Owl monkey astrocytoma cells in culture spontaneously produce infectious JC virus which demonstrates altered biological properties." J Virol 61(5): 1435-41.

Marra, C. M., N. Rajicic, et al. (2002). "A pilot study of cidofovir for progressive multifocal leukoencephalopathy in AIDS." Aids 16(13): 1791-7.

Pham, Y. T., F. Nosten, et al. (1999). "Cerebral uptake of mefloquine enantiomers in fatal cerebral malaria." Int J Clin Pharmacol Ther 37(1): 58-61.

Pho, M. T., A. Ashok, et al. (2000). JC Virus Enters Human Glial Cells by Clathrin-Dependent Receptor-Mediated Endocytosis. 74: 2288-2292.

Royal, W., 3rd, B. Dupont, et al. (2003). "Topotecan in the treatment of acquired immunodeficiency syndrome-related progressive multifocal leukoencephalopathy." J Neurovirol 9(3): 411-9.

Shitrit, D., L. Nirit, et al. (2003). "Progressive multifocal leukoencephalopathy in a lung transplant recipient." J Heart Lung Transplant 22(8): 946-50.

Vacante, D. A., R. Traub, et al. (1989). "Extension of JC virus host range to monkey cells by insertion of a simian virus 40 enhancer into the JC virus regulatory region." Virology 170(2): 353-61.

Weiss, S. M., K. Benwell, et al. (2003). "Discovery of nonxanthine adenosine A2A receptor antagonists for the treatment of Parkinson's disease." Neurology 61(11 Suppl 6): S 101-6.

Zhang, J. H., T. D. Chung, et al. (1999). "A Simple Statistical Parameter for Use in Evaluation and Validation of High Throughput Screening Assays." J Biomol Screen 4(2): 67-73.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

What is claimed is:

1. A method of inhibiting polyomavirus replication in a subject, the method comprising administering a composition to a subject suspected of having a polyomavirus infection, wherein the composition comprises fusidic acid in an amount sufficient to inhibit polyomavirus replication in the subject.

2. The method of claim 1, wherein the polyomavirus is JC virus.

3. The method of claim 1, wherein the polyomavirus is BK virus.

4. The method of claim 1, wherein the subject has been identified as having a JC virus infection of the central nervous system (CNS).

5. The method of claim 1, wherein the subject has been identified as having a BK virus infection of the kidney.

6. The method of claim 1, wherein the subject is undergoing, or has been undergoing, an immunomodulatory treatment.

7. The method of claim 6, wherein the immunomodulatory treatment comprises the administration of a VLA-4 antibody.

8. The method of claim 7, wherein the VLA-4 antibody is natalizumab.

* * * * *